US008744776B2

(12) United States Patent
Wu et al.

(10) Patent No.: US 8,744,776 B2
(45) Date of Patent: *Jun. 3, 2014

(54) METHOD FOR DETERMINING ANALYTE CONCENTRATION BASED ON COMPLEX INDEX FUNCTIONS

(75) Inventors: Huan-Ping Wu, Granger, IN (US); Sung-Kwon Jung, Granger, IN (US)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/153,793

(22) Filed: Jun. 6, 2011

(65) Prior Publication Data

US 2011/0297554 A1 Dec. 8, 2011

Related U.S. Application Data

(63) Continuation of application No. PCT/US2009/067150, filed on Dec. 8, 2009.

(60) Provisional application No. 61/120,525, filed on Dec. 8, 2008.

(51) Int. Cl.
*G01N 33/48* (2006.01)

(52) U.S. Cl.
USPC .......................................................... 702/19

(58) Field of Classification Search
None
See application file for complete search history.

(56) References Cited

U.S. PATENT DOCUMENTS

| | | | |
|---|---|---|---|
| 4,431,004 A | 2/1984 | Bessman et al. |
| 4,750,496 A | 6/1988 | Reinhart et al. |
| 5,243,516 A | 9/1993 | White |
| 5,366,609 A | 11/1994 | White et al. |
| 5,395,504 A | 3/1995 | Saurer et al. |
| 5,508,171 A | 4/1996 | Walling et al. |
| 5,620,579 A | 4/1997 | Genshaw et al. |
| 5,653,863 A | 8/1997 | Genshaw et al. |
| 5,723,284 A | 3/1998 | Ye |
| 5,798,031 A | 8/1998 | Charlton et al. |
| 6,120,676 A | 9/2000 | Heller et al. |
| 6,153,069 A | 11/2000 | Pottgen et al. |
| 6,233,471 B1 | 5/2001 | Berner et al. |
| 6,275,717 B1 | 8/2001 | Gross et al. |
| 6,391,645 B1 | 5/2002 | Huang et al. |
| 6,413,411 B1 | 7/2002 | Pottgen et al. |
| 6,475,372 B1 | 11/2002 | Ohara et al. |
| 6,576,117 B1 | 6/2003 | Iketaki et al. |
| 6,645,368 B1 | 11/2003 | Beaty et al. |
| 6,797,150 B2 | 9/2004 | Kermani et al. |
| 6,824,670 B2 | 11/2004 | Tokunaga et al. |
| 7,122,111 B2 | 10/2006 | Tokunaga et al. |
| 7,132,041 B2 | 11/2006 | Deng et al. |
| 7,351,323 B2 | 4/2008 | Iketaki et al. |
| 7,501,052 B2 | 3/2009 | Iyenga et al. |
| 7,517,439 B2 | 4/2009 | Harding et al. |
| 2004/0072158 A1 | 4/2004 | Henkens et al. |
| 2004/0079652 A1 | 4/2004 | Vreke et al. |
| 2004/0256248 A1 | 12/2004 | Burke et al. |
| 2004/0260511 A1 | 12/2004 | Burke et al. |
| 2005/0176153 A1 | 8/2005 | O'hara et al. |
| 2007/0231914 A1 | 10/2007 | Deng et al. |
| 2008/0248581 A1 | 10/2008 | Chu et al. |

FOREIGN PATENT DOCUMENTS

| | | |
|---|---|---|
| EP | 1742045 | 1/2007 |
| JP | 2005147990 | 6/2005 |
| WO | 9614026 | 10/1995 |
| WO | 9858250 | 12/1998 |
| WO | 0121827 | 3/2001 |
| WO | 2006042304 | 4/2006 |
| WO | 2006079797 | 8/2006 |
| WO | 2007013915 | 2/2007 |
| WO | 2007014231 | 2/2007 |
| WO | 2007040913 | 4/2007 |
| WO | 2007133985 | 11/2007 |
| WO | 2009108239 | 9/2009 |

OTHER PUBLICATIONS

International Searching Authority, "International Search Report and Written Opinion for PCT/US2006/028013", Dec. 6, 2006, Publisher: European Patent Office, Published in: EP.
International Searching Authority, "International Search Report and Written Opinion for PCT/US2007/068320", Oct. 19, 2007, Publisher: European Patent Office, Published in: EP.
International Searching Authority, "International Search Report and Written Opinion for PCT/US2008/085768", Sep. 28, 2009, Publisher: European Patent Office, Published in: EP.
International Searching Authority, "International Search Report and Written Opinion for PCT/US2009/067150", Apr. 19, 2010, Publisher: European Patent Offce.
Gunasingham, et al., "Pulsed amperometric detection of glucose using a mediated enzyme electrode", "Journal of Electroanalytical Chemistry", 1990, pp. 349-362, vol. 287, No. 2.
Lin, et al., "Reduction of the Interferences of Biochemicals and Hematrocrit Ratio on the Determination of Whole Blood Glucose Using", "Anal. Bioanal. Chem.", 2007, pp. 1623-1631, vol. 289.
Panteleon, et al., "The Role of the Independent Variable to Gluscose Sensor Calibration", "Diabetes Technology & Therapeutics", 2003, pp. 401-441, vol. 5, No. 3.

*Primary Examiner* — Pablo S Whaley
(74) *Attorney, Agent, or Firm* — Blanchard & Associates

(57) ABSTRACT

A biosensor system determines analyte concentration from an output signal generated from a light-identifiable species or a redox reaction of the analyte. The biosensor system adjusts a correlation for determining analyte concentrations from output signals or determined analyte concentrations with one or more complex index function extracted from the output signals or from other sources. The complex index functions determine at least one slope deviation value, ΔS, or normalized slope deviation from one or more error parameters. The slope-adjusted correlation between analyte concentrations and output signals may be used to determine analyte concentrations having improved accuracy and/or precision from output signals including components attributable to bias.

19 Claims, 9 Drawing Sheets

METHOD FOR DETERMINING ANALYTE CONCENTRATION BASED ON COMPLEX INDEX FUNCTIONS

REFERENCE TO RELATED APPLICATIONS

This application is a continuation of PCT Application No. PCT/US2009/067150 entitled "Complex Index Functions" filed Dec. 8, 2009, which claims the benefit of U.S. Provisional Application No. 61/120,525 entitled "Complex Index Functions" filed Dec. 8, 2008, which are incorporated by reference in their entirety.

BACKGROUND

Biosensor systems provide an analysis of a biological fluid, such as whole blood, serum, plasma, urine, saliva, interstitial, or intracellular fluid. Typically, the systems include a measurement device that analyzes a sample contacting a test sensor. The sample usually is in liquid form and in addition to being a biological fluid, may be the derivative of a biological fluid, such as an extract, a dilution, a filtrate, or a reconstituted precipitate. The analysis performed by the biosensor system determines the presence and/or concentration of one or more analytes, such as alcohol, glucose, uric acid, lactate, cholesterol, bilirubin, free fatty acids, triglycerides, proteins, ketones, phenylalanine or enzymes, in the biological fluid. The analysis may be useful in the diagnosis and treatment of physiological abnormalities. For example, a diabetic individual may use a biosensor system to determine the glucose level in whole blood for adjustments to diet and/or medication.

Biosensor systems may be designed to analyze one or more analytes and may use different volumes of biological fluids. Some systems may analyze a single drop of whole blood, such as from 0.25-15 microliters ($\mu L$) in volume. Biosensor systems may be implemented using bench-top, portable, and like measurement devices. Portable measurement devices may be hand-held and allow for the identification and/or quantification of one or more analytes in a sample. Examples of portable measurement systems include the Ascensia® Breeze® and Elite® meters of Bayer HealthCare in Tarrytown, N.Y., while examples of bench-top measurement systems include the Electrochemical Workstation available from CH Instruments in Austin, Tex.

Biosensor systems may use optical and/or electrochemical methods to analyze the biological fluid. In some optical systems, the analyte concentration is determined by measuring light that has interacted with or been absorbed by a light-identifiable species, such as the analyte or a reaction or product formed from a chemical indicator reacting with the analyte. In other optical systems, a chemical indicator fluoresces or emits light in response to the analyte when illuminated by an excitation beam. The light may be converted into an electrical output signal, such as current or potential, which may be similarly processed to the output signal from an electrochemical method. In either optical system, the system measures and correlates the light with the analyte concentration of the sample.

In light-absorption optical systems, the chemical indicator produces a reaction product that absorbs light. A chemical indicator such as tetrazolium along with an enzyme such as diaphorase may be used. Tetrazolium usually forms formazan (a chromagen) in response to the redox reaction of the analyte. An incident input beam from a light source is directed toward the sample. The light source may be a laser, a light emitting diode, or the like. The incident beam may have a wavelength selected for absorption by the reaction product. As the incident beam passes through the sample, the reaction product absorbs a portion of the incident beam, thus attenuating or reducing the intensity of the incident beam. The incident beam may be reflected back from or transmitted through the sample to a detector. The detector collects and measures the attenuated incident beam (output signal). The amount of light attenuated by the reaction product is an indication of the analyte concentration in the sample.

In light-generated optical systems, the chemical detector fluoresces or emits light in response to the analyte redox reaction. A detector collects and measures the generated light (output signal). The amount of light produced by the chemical indicator is an indication of the analyte concentration in the sample.

In electrochemical biosensor systems, the analyte concentration is determined from an electrical signal generated by an oxidation/reduction or redox reaction of the analyte or a species responsive to the analyte when an input signal is applied to the sample. The input signal may be a potential or current and may be constant, variable, or a combination thereof such as when an AC signal is applied with a DC signal offset. The input signal may be applied as a single pulse or in multiple pulses, sequences, or cycles. An enzyme or similar species may be added to the sample to enhance the electron transfer from a first species to a second species during the redox reaction. The enzyme or similar species may react with a single analyte, thus providing specificity to a portion of the generated output signal. A mediator may be used to maintain the oxidation state of the enzyme.

Electrochemical biosensor systems usually include a measurement device having electrical contacts that connect with electrical conductors in the test sensor. The conductors may be made from conductive materials, such as solid metals, metal pastes, conductive carbon, conductive carbon pastes, conductive polymers, and the like. The electrical conductors typically connect to working, counter, reference, and/or other electrodes that extend into a sample reservoir. One or more electrical conductors also may extend into the sample reservoir to provide functionality not provided by the electrodes.

The measurement device applies an input signal through the electrical contacts to the electrical conductors of the test sensor. The electrical conductors convey the input signal through the electrodes into the sample present in the sample reservoir. The redox reaction of the analyte generates an electrical output signal in response to the input signal. The electrical output signal from the strip may be a current (as generated by amperometry or voltammetry), a potential (as generated by potentiometry/galvanometry), or an accumulated charge (as generated by coulometry). The measurement device may have the processing capability to measure and correlate the output signal with the presence and/or concentration of one or more analytes in the biological fluid.

In coulometry, a potential is applied to the sample to exhaustively oxidize or reduce the analyte. A biosensor system using coulometry is described in U.S. Pat. No. 6,120,676. In amperometry, an electrical signal of constant potential (voltage) is applied to the electrical conductors of the test sensor while the measured output signal is a current. Biosensor systems using amperometry are described in U.S. Pat. Nos. 5,620,579; 5,653,863; 6,153,069; and 6,413,411. In voltammetry, a varying potential is applied to a sample of biological fluid. In gated amperometry and gated voltammetry, pulsed inputs may be used as described in WO 2007/013915 and WO 2007/040913, respectively.

In many biosensor systems, the test sensor may be adapted for use outside, inside, or partially inside a living organism.

When used outside a living organism, a sample of the biological fluid may be introduced into a sample reservoir in the test sensor. The test sensor may be placed in the measurement device before, after, or during the introduction of the sample for analysis. When inside or partially inside a living organism, the test sensor may be continually immersed in the sample or the sample may be intermittently introduced to the strip. The test sensor may include a reservoir that partially isolates a volume of the sample or be open to the sample. When open, the strip may take the form of a fiber or other structure placed in contact with the biological fluid. Similarly, the sample may continuously flow through the strip, such as for continuous monitoring, or be interrupted, such as for intermittent monitoring, for analysis.

Biosensor systems may provide an output signal during the analysis of the biological fluid that includes one or multiple errors. These errors may be reflected in an abnormal output signal, such as when one or more portions or the entire output signal is non-responsive or improperly responsive to the analyte concentration of the sample. These errors may be from one or more contributors, such as the physical characteristics of the sample, the environmental aspects of the sample, the operating conditions of the system, interfering substances, and the like. Physical characteristics of the sample include hematocrit (red blood cell) concentration and the like. Environmental aspects of the sample include temperature and the like.

The measurement performance of a biosensor system is defined in terms of accuracy and/or precision. Increases in accuracy and/or precision provide for an improvement in measurement performance, a reduction in the bias, of the system. Accuracy may be expressed in terms of bias of the sensor system's analyte reading in comparison to a reference analyte reading, with larger bias values representing less accuracy. Precision may be expressed in terms of the spread or variance of the bias among multiple analyte readings in relation to a mean. Bias is the difference between one or more values determined from the biosensor system and one or more accepted reference values for the analyte concentration in the biological fluid. Thus, one or more errors in the analysis results in the bias of the determined analyte concentration of a biosensor system.

Bias may be expressed in terms of "absolute bias" or "percent bias". Absolute bias may be expressed in the units of the measurement, such as mg/dL, while percent bias may be expressed as a percentage of the absolute bias value over the reference value. Under the ISO standard, absolute bias is used to express error in glucose concentrations less than 75 mg/dL, while percent bias is used to express error in glucose concentrations of 75 mg/dL and higher. The term "combined bias" (expressed as bias/%-bias) represents absolute bias for glucose concentrations less than 75 mg/dL and percent bias for glucose concentrations of 75 mg/dL and higher. Accepted reference values for analyte concentrations may be obtained with a reference instrument, such as the YSI 2300 STAT PLUS™ available from YSI Inc., Yellow Springs, Ohio.

Hematocrit bias refers to the difference between the reference glucose concentration obtained with a reference instrument and an experimental glucose reading obtained from a biosensor system for samples containing differing hematocrit levels. The difference between the reference and values obtained from the system results from the varying hematocrit level between specific whole blood samples and may be generally expressed as a percentage by the following equation: % Hct-Bias=$100\% \times (G_m - G_{ref})/G_{ref}$, where $G_m$ and $G_{ref}$ are the determined glucose and reference glucose concentration readings, respectively, for any hematocrit level. The larger the absolute value of the % Hct-bias, the more the hematocrit level of the sample (expressed as % Hct: the percentage of red blood cell volume/sample volume) is reducing the accuracy and/or precision of the determined glucose concentration. For example, if whole blood samples containing identical glucose concentrations, but having hematocrit levels of 20, 40, and 60%, are analyzed, three different glucose readings will be reported by a system based on one set of calibration constants (slope and intercept of the 40% hematocrit containing whole blood sample, for instance). "Hematocrit sensitivity" is an expression of the degree to which changes in the hematocrit level of a sample affect the bias values for an analysis. Hematocrit sensitivity may be defined as the numerical values of the combined biases per percent hematocrit, thus bias/%-bias per % Hct.

Temperature bias refers to the difference between an analyte concentration obtained at a reference temperature and an analyte concentration obtained at a different experimental temperature for the same sample. The difference between the analyte concentration obtained at the reference temperature and that obtained from the different experimental temperature may be generally expressed as a percentage by the following equation: % Temp-Bias=$100\% \times (A_{mTemp} - A_{RefTemp})/A_{RefTemp}$, where $A_{mTemp}$ and $A_{RefTemp}$ are the analyte concentrations at the experimental and reference temperatures, respectively, for the sample. The larger the absolute value of the % Temp-bias, the more the temperature difference is reducing the accuracy and/or precision of the glucose concentration determined at the different experimental temperature. "Temperature sensitivity" is an expression of the degree to which changes in the temperature at which the analysis is performed affect the bias values for an analysis. Temperature sensitivity may be defined as the numerical values of the combined biases per degree of temperature, thus %-bias/° C. Temperature sensitivity also may be defined as slope deviation per degree of temperature, thus $\Delta S/°$ C.

Many biosensor systems include one or more methods to correct errors associated with an analysis. The concentration values obtained from an analysis with an error may be inaccurate. Thus, the ability to correct these analyses may increase the accuracy and/or precision of the concentration values obtained. An error correction system may compensate for one or more errors, such as a sample temperature or a sample hematocrit level, which are different from a reference temperature or a reference hematocrit value.

Some biosensor systems have an error correction system that compensates for different hematocrit concentrations in the sample. Various methods and techniques have been proposed to reduce the bias of the hematocrit effect on glucose measurements. Some methods use the ratio of currents from a forward and a reverse potential pulse to compensate for the hematocrit effect. Other methods have been proposed to reduce the bias of the hematocrit effect, including using silica particles to filter red blood cells from the electrode surface or using wide electrode spacing in combination with mesh layers to distribute blood throughout the test sensor.

Some biosensor systems have an error correction system that compensates for temperature. Such error correction systems typically alter a determined analyte concentration for a particular reference temperature in response to an instrument or sample temperature. A number of biosensor systems compensate for temperature error by correcting the output signal prior to calculating the analyte concentration from a correlation equation. Other biosensor systems compensate for temperature error by correcting the analyte concentration calculated from the correlation equation. Generally, conventional methods of temperature compensation look at the effect of temperature on a specific parameter, not the overall effect the temperature error has on the bias of the analysis. Biosensor systems having error detection and/or compensation systems for the sample temperature are described in U.S. Pat. Nos. 4,431,004; 4,750,496; 5,366,609; 5,395,504; 5,508,171; 6,391,645; and 6,576,117.

Some biosensor systems have an error correction system that compensates for interferents and other contributors. Such error correction systems typically use an electrode lacking one or more of the working electrode reagents to allow for the subtraction of a background interferent signal from the working electrode signal.

While conventional error compensation systems balance various advantages and disadvantages, none are ideal. Conventional systems usually are directed to detect and respond to a particular type of error, either temperature or hematocrit, for example. Such systems typically do not have the ability to compensate for multiple error sources. These systems generally also lack the ability to alter the compensation for the error based on the output signal from a specific sample. Consequently, conventional biosensor systems may provide analysis results having determined analyte concentration values outside a desired performance limit.

Accordingly, there is an ongoing need for improved biosensor systems, especially those that may provide increasingly accurate and/or precise determination of the concentration of the analyte in the sample. The systems, devices, and methods of the present invention overcome at least one of the disadvantages associated with conventional biosensor systems.

SUMMARY

The present invention provides a biosensor system that adjusts a relation for determining analyte concentrations in a biological sample from output signals with one or more complex index functions responsive to one or more errors that could bias the determined analyte concentrations. The bias may be represented by slope deviations, ΔS values, and normalized slope deviations obtained from one or more error parameters. The ΔS values represent slope deviations determined with one or more complex index functions from the error parameters. The complex index functions include at least two terms modified by weighing coefficients. The terms may include error parameters extracted from or independent of the output signals.

In a method for determining an analyte concentration in a sample, an output signal value responsive to the concentration of the analyte in the sample is generated. At least one ΔS value from at least one error parameter is determined, and the at least one output signal value is compensated with at least one reference correlation and at least one ΔS value to determine the analyte concentration in the sample. The at least one ΔS value may be determined from a predictor function f(predictor). The f(predictor) includes an index function and relates at least one error parameter to ΔS. The reaction may be an electrochemical redox reaction.

In a method for determining complex index functions from error parameters, at least one error parameter responsive to the percent bias in a determined analyte concentration in a sample is determined. The at least one error parameter is related to at least one ΔS value with at least one complex index function, the at least one ΔS value representing the difference in slope between the slope from a reference correlation and a hypothetical slope of a line for the output signal value that would provide an analyte concentration in the sample without bias. The complex index functions includes the at least one error parameter incorporated as a term modified by a weighing coefficient.

In a method for selecting terms for inclusion in a complex index function, multiple error parameters are selected as terms for potential inclusion in the complex index function. First exclusion values are determined for each selected term. One or more exclusion tests are applied to the exclusion values to identify one or more terms to exclude from the complex index function. After the exclusion of at least one term, second exclusion values are determined for the remaining terms. If the second exclusion values do not identify remaining terms for exclusion from the complex index function under the one or more exclusion texts, the remaining terms are included in the complex index function.

In a method for determining a complex index function from hematocrit-adjusted and donor blood samples for use in a measurement device, the experimental glucose concentration of multiple hematocrit-adjusted blood samples having known reference glucose concentrations at multiple environmental conditions is determined with multiple test sensors. The slope and intercept of a reference correlation for the multiple test sensors is determined from the determined and known glucose concentrations at a reference temperature and at a reference % Hct. The reference glucose concentration is determined for multiple donor blood samples. The multiple hematocrit-adjusted blood sample glucose concentration data may be combined with the multiple donor blood sample glucose concentration data. Terms are selected from the data for one or more output signal value. Terms also may be selected for one or more physical characteristic, environmental condition, concentration value, and the like. Weighing coefficients are determined for the terms, in addition to any coefficients. The complex index function is determined from the combination of selected terms, corresponding weighing coefficients, and any constants.

A biosensor system for determining an analyte concentration in a sample includes a measurement device and a test sensor. The measurement device has a processor connected to a sensor interface and to a storage medium. The test sensor has a sample interface adjacent to a reservoir formed by the sensor. The processor determines an output signal value responsive to the concentration of the analyte in the sample from the sensor interface. The processor determines at least one ΔS value from an error parameter and compensates the output signal value with the at least one ΔS value and at least one reference correlation present in the storage medium.

A biosensor system adjusts a correlation between analyte concentrations and output signals with at least one ΔS value in response to error parameters. The processor determines an analyte concentration from the slope-adjusted correlation in response to an output signal from the sample interface.

In another method for determining an analyte concentration in a sample, one or more output signals are generated from a sample. At least one complex index function is determined, where the complex index function is responsive to more than one error parameter. The analyte concentration in the sample is determined from the output signals in response to the at least one complex index function.

Other systems, methods, features, and advantages of the invention will be, or will become, apparent to one with skill in the art upon examination of the following figures and detailed description. It is intended that all such additional systems, methods, features and advantages be included within this description, be within the scope of the invention, and be protected by the claims that follow.

BRIEF DESCRIPTION OF THE DRAWINGS

The invention may be better understood with reference to the following drawings and description. The components in the figures are not necessarily to scale, emphasis instead being placed upon illustrating the principles of the invention.

DETAILED DESCRIPTION

A biosensor system adjusts a correlation for determining analyte concentrations in a biological sample from output signals with complex index functions extracted from intermediate signals of the output signals or from other sources. The analyte may generate the output signals in response to a light-identifiable species or a redox reaction. The intermediate signals may be one or more portions of the output signals or the like. Predictor functions including at least one complex index function adjust the correlation for determining analyte concentrations from the output signals for one or more errors in the analyses. Predictor functions including at least one complex index function also may be used to correct an analyte concentration including errors. Such errors can result in bias, thus reduced accuracy and/or precision, of the determined analyte concentrations. In addition to the compensation system providing substantial benefits when analyzing complex biological samples, the compensation system may be used to improve the measurement performance of other types of analysis.

Complex index functions include combinations of terms modified by weighing coefficients. The terms included in the complex index function may be selected with one or more exclusion tests. Predictor functions and/or complex index functions correspond to the bias/%-bias in the correlation between the analyte concentrations and the output signals due to one or more errors in the analysis. The %-bias in the correlation may be represented by one or more $\Delta S$ values obtained from one or more error parameters. The $\Delta S$ values represent slope deviations of the correlation between analyte concentrations and output signals determined from one or more error parameters. Thus, the more closely a predictor or complex index function correlates with $\Delta S$ ($\Delta S=f(CIndex)$), the better the function is at correcting error in the analysis.

Complex index functions corresponding to the slope or change in slope may be normalized to reduce the statistical effect of changes in the output signals, improve the differentiation in variations of the output signals, standardize the measurements of the output signals, a combination thereof, or the like. Since the slope deviation may be normalized, a complex index function also may be expressed in terms of $\Delta S/S=f(CIndex)$. The adjusted correlation may be used to determine analyte concentrations in the sample from the output signals or may be used to correct analyte concentrations and may provide improved measurement performance in comparison to conventional biosensors. A more detailed treatment of error correction using index functions and $\Delta S$ values may be found in Intl. Pub. No. WO 2009/108239, filed Dec. 6, 2008, entitled "Slope-Based Compensation."

Figure 1A:
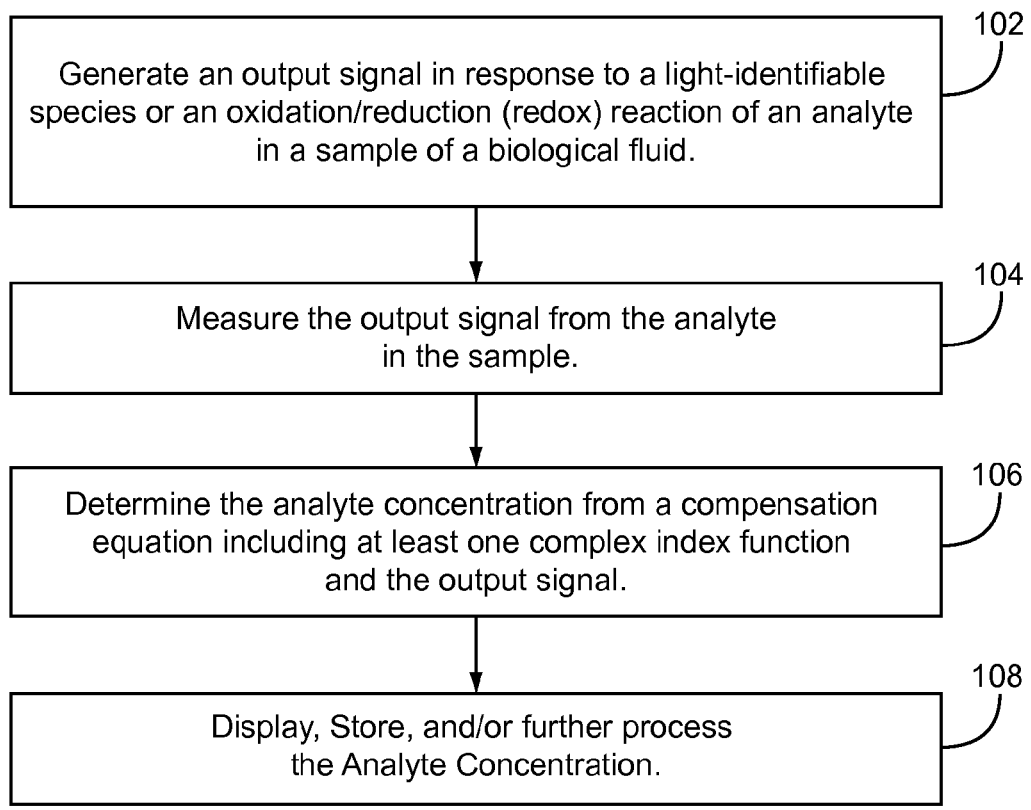
FIG. 1A represents a method for determining an analyte concentration in a sample.

FIG. 1A represents a method for determining an analyte concentration in a sample of a biological fluid. In 102, the biosensor system generates an output signal in response to either a light-identifiable species or an oxidation/reduction (redox) reaction of an analyte in a sample of a biological fluid. In 104, the biosensor system measures the output signal. In 106, the analyte concentration is determined from a compensation equation including at least one complex index function and the output signal. In 110, the analyte concentration may be displayed, stored for future reference, and/or used for additional calculations.

In 102 of FIG. 1A, the biosensor system generates an output signal in response to a light-identifiable species or an oxidation/reduction (redox) reaction of an analyte in a sample of a biological fluid. The output signal may be generated using an optical sensor system, an electrochemical sensor system, or the like.

In 104 of FIG. 1A, the biosensor system measures the output signal generated by the analyte in response to the input signal applied to the sample, such as from a redox reaction of the analyte. The system may measure the output signal continuously or intermittently. For example, the biosensor system may measure the output signal intermittently during the pulses of a gated amperometric input signal, resulting in multiple current values recorded during each pulse. The system may show the output signal on a display and/or may store the output signal or portions of the output signal in a memory device.

Figure 2:
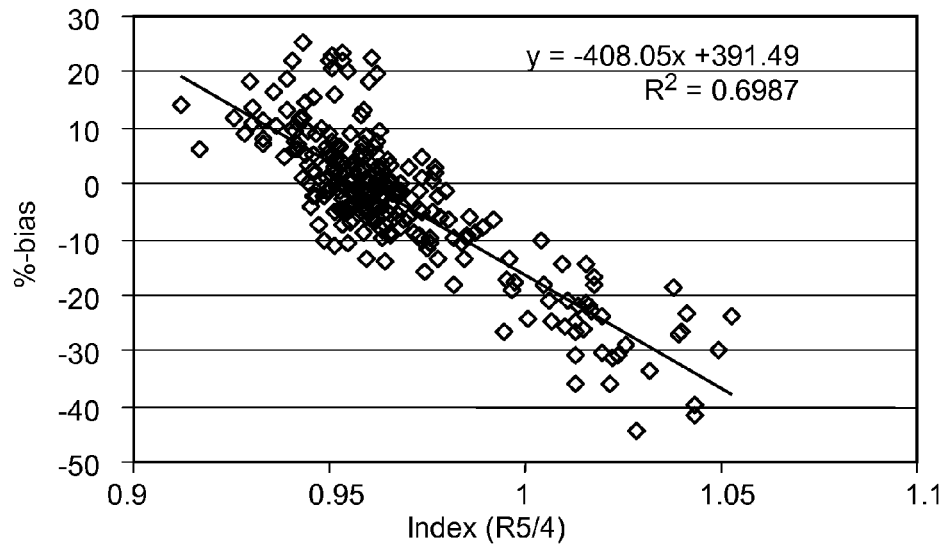
FIG. 2 depicts the correlation between %-bias and an index function based on a ratio parameter.

In 106 of FIG. 1A, the analyte concentration of the sample may be determined from a compensation equation including at least one complex index function and the output signal. The complex index function may form part of a predictor function. FIG. 2 depicts the correlation between %-bias and an index function based on a ratio parameter (R5/4). The ratio parameter, R5/4, represents the relationship between the currents generated by the analyte in response to the $4^{th}$ and $5^{th}$ pulses of a gated amperometry pulse sequence including 7 pulses. Other ratio parameters and index functions may be used. Thus, the %-bias of a measured analyte concentration in a biological fluid, such as glucose in whole blood, may be determined from or correlated with the output signals of the analysis, such as the intermediate currents generated by the analyte in response to a gated amperometry sequence.

The relationship between %-bias and a predictor function may be represented as follows:

$$\text{\%-bias} = f(\text{predictor}) \quad \text{(Equation 1)},$$

where %-bias equals $(\Delta A/A_{ref})*100\%$ and f(predictor) equals $a_1*f(\text{Index})+a_0$. $\Delta A$ is the difference between the measured or calculated analyte concentration, $A_{cal}$, and a reference analyte concentration, $A_{ref}$ (a known analyte concentration in a biological sample). f(Index) may be a single error parameter, a combination of error parameters, or other values. Thus, substituting terms for Equation 1 results in the following relationship between %-bias and an index function:

$$(\Delta A/A_{ref})*100\% = a_1*f(\text{Index})+a_0 \quad \text{(Equation 2)}.$$

Rearranging the terms of Equation 2 results in the following relationship:

$$\Delta A = A_{ref}*(a_1*f(\text{Index})+a_0)/100 \quad \text{(Equation 3)}.$$

A compensation may be expressed as follows:

$$A_{corr} = A_0 + \Delta A \quad \text{(Equation 4)}.$$

Where $A_{corr}$ is a corrected or compensation analyte compensation and $A_0$ is an initial analyte value from the analysis. While $\Delta A$ may be obtained from Equation 3, $A_{ref}$ in Equation 3 may not be available during the analysis of a biological sample. However, the initial analyte value, $A_0$, may be used from the analysis in place of $A_{ref}$. Thus, Equation 3 may be approximated by the following relationship:

$$\Delta A \cong A_0*(a_1*\text{Index}+a_0)/100 \quad \text{(Equation 5)}.$$

Finally, substituting Equation 5 into Equation 4 results in the following relationship:

$$A_{corr} = A_0 + A_0*(a_1*\text{Index}+a_0)/100 = A_0*[1+(a_1*\text{Index}+a_0)/100] \quad \text{(Equation 6)}.$$

From Equation 6, the difference between the measured analyte concentration and a reference analyte concentration, $\Delta A$, is based on an initial analyte value, $A_0$, which may be biased due to one or more errors in the analysis. Thus, there is no reference point or value upon which to base the compensation of the measured analyte concentration. While these and other equations presented throughout the application and claims may include an "=" sign, the sign is used to represent equivalence, relationship, prediction, or the like.

The %-bias in the correlation of analyte concentrations with output signals also may be represented by one or more slope deviations, $\Delta S$, obtained from one or more error parameters. Error containing portions of output signals are reflected in the deviation between the hypothetical slope of the output signals and the slope of a reference correlation. By determining one or more $\Delta S$ values reflecting this deviation in slope from one or more error parameters, the measurement performance of an analysis may be increased. One or more $\Delta S$ values for an analysis may be determined from one or more error parameters. The relationship between $\Delta S$ values and the value of one or more error parameters may be described by an index function. Index functions, in addition to reference correlation equations, may be pre-determined and stored in the biosensor system. Error parameter values may be determined before, during, or after the analysis.

The slope compensation equation uses output signal values to provide a compensated analyte concentration. The slope compensation equation also may use other values. The slope compensation equation compensates for error by adjusting a reference correlation between output signals and known analyte concentrations to provide a compensated or corrected analyte concentration.

The slope compensation equation may be represented as follows:

$$A_{corr} = \frac{i - Int}{S_{cal} + \Delta S}, \quad \text{(Equation 7)}$$

where $A_{corr}$ is the corrected analyte concentration, i is a value of the output signal from a biosensor system, Int is the intercept from a reference correlation equation, $S_{cal}$ is the slope from the reference correlation equation, and $\Delta S$ represents the deviation in slope between $S_{cal}$ and a hypothetical slope of a line ($S_{hyp}$) for the output signal value that provides an analyte concentration of the sample without error. The Int and $S_{cal}$ values for the reference correlation equation may be implemented as a program number assignment (PNA) table, another look-up table, or the like in the biosensor system. Other slope compensation equations including at least one $\Delta S$ value and the output signal may be used.

Equation 7 is a representation of the corrected analyte concentration determined using the slope deviation $\Delta S$, where $\Delta S$ is essentially the total slope deviation related to essentially the total error associated with the analyte analysis. The total slope deviation may be caused by one or more error sources. Equation 7 may be used with any signal having a substantially linear response to analyte concentration. Equation 7 may be used with other signals, such as signals that are near or partially linear. While $\Delta S$ is responsive to one or more errors in the output signal, i represents the error containing portions of the output signal not responsive to the analyte concentration of the sample. Thus, $S_{hyp}=S_{cal}+\Delta S$. One or more values for Int and $S_{cal}$ may be stored in the biosensor system for comparison with the output signal i to determine $A_{corr}$ for the sample.

If the value of $\Delta S$ is determined experimentally from samples and substituted into Equation 7, the bias in the determined analyte concentrations of those samples will be fully compensated. Alternatively, if $\Delta S$ is substituted with a predictor function, then the ability of the compensation equation to correct bias in the determined analyte concentration will depend on how well the value generated from the predictor function correlates with $\Delta S$. In Equation 7, a predictor function, f(predictor), may be substituted for $\Delta S$. Thus, Equation 7 may be rewritten as follows:

$$A_{corr} = \frac{i - Int}{S_{cal} + \Delta S} = \frac{i - Int}{S_{cal} + f(\text{predictor})} = \frac{i - Int}{S_{cal} + b_1*f(CIndex) + b_0}. \quad \text{(Equation 8)}$$

While the predictor function, f(predictor), may have the general form of $b_1*f(CIndex)+b_0$, where f(CIndex) is a complex index function, other values or indices may be used in combination with the f(CIndex) to provide f(predictor). For example, the complex index function could be used with or without one or both of the $b_1$ and $b_0$ values to provide the predictor function. Multiple complex index functions also may be combined to provide the f(predictor), and thus, the corrected analyte concentration of the sample.

For the theoretical situation where $\Delta S$ and the complex index function perfectly correlate, $b_1$ (representing slope) and $b_0$ (representing intercept) are one and zero, respectively. When the predictor function is approximating $\Delta S$, the theoretical value of one may be used in place of $b_1$ when $b_1=1\pm0.2$, preferably one may be used in place of $b_1$ when $b_1=1\pm0.15$, and more preferably one may be used in place of $b_1$ when $b_1=1\pm0.1$. When the predictor function is approximating $\Delta S$, the theoretical value of zero may be used in place of $b_0$ when $b_0=0\pm0.3$, preferably zero may be used in place of $b_0$ when $b_0=0\pm0.2$, and more preferably zero may be used in place of $b_0$ when $b_0=0\pm0.1$. Other deviation cut-offs may be used to determine when the theoretical values for $b_1$, $b_0$, or both may be used. In addition to substituting $b_1$ and/or $b_0$ with the theoretical values 1 and 0, predetermined values from a look-up table and the like may be substituted based on the same or other deviation cut-offs.

In 108 of FIG. 1A, the corrected analyte concentration value may be displayed, stored for future reference, and/or used for additional calculations.

Figure 3:
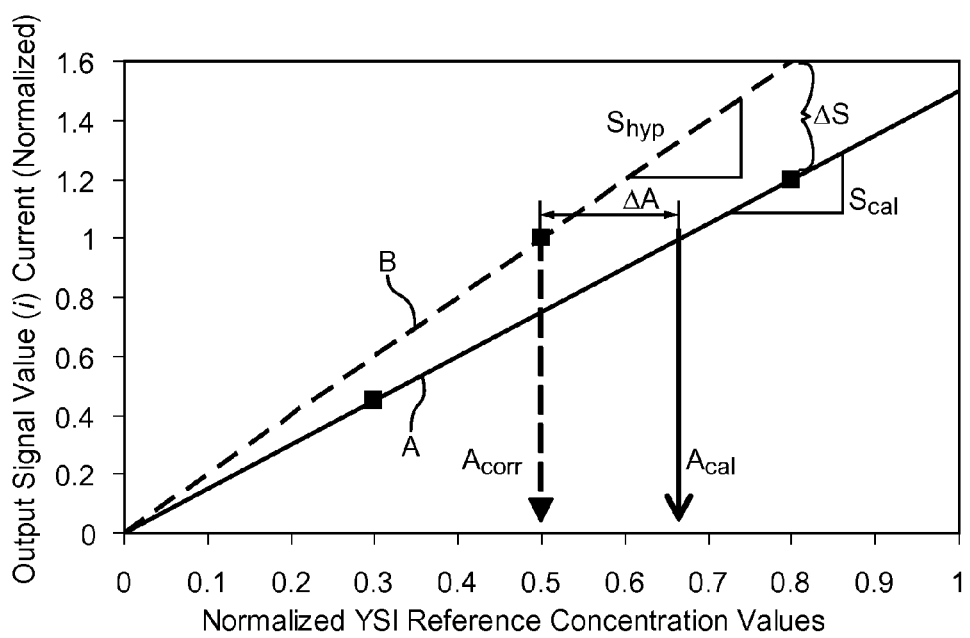
FIG. 3 depicts the relationship between $S_{cal}$, $S_{hyp}$, $\Delta S$, $A_{corr}$, $A_{cal}$, and $\Delta A$.

FIG. 3 shows the relationship between $S_{cal}$, $S_{hyp}$, $\Delta S$, $A_{corr}$, $A_{cal}$, and $\Delta A$. Line A represents a reference correlation having a slope $S_{cal}$ and relating an output signal in the form of current values from a biosensor system to analyte concentration values obtained from a YSI or other reference instrument for the samples. When used during the analysis of a sample by a biosensor system, the reference correlation of Line A may include output signal current values having one or more errors that may provide an inaccurate and/or imprecise analyte concentration value. Line B represents an error-compensated correlation having a slope $S_{hyp}$ and relating current values obtained from the system with the sample analyte concentration values as obtained from the reference instrument. The error-compensated correlation has been adjusted or modified to reduce or substantially eliminate the one or more errors. $\Delta S$ is the difference in slope between these correlation lines. $\Delta A$ is the difference between the uncompensated or uncorrected ($A_{cal}$) and error compensated or corrected ($A_{corr}$) determined analyte concentration values.

Without compensation or correction, a specific output signal value will provide a different sample analyte concentration from the $S_{cal}$ reference correlation line than from the $S_{hyp}$ error-compensated line. The $A_{corr}$ value obtained from the $S_{hyp}$ error-compensated line provides a more accurate value of the analyte concentration in the sample. Thus, Equation 7 translates a current value, $S_{cal}$, and Int into the compensated analyte concentration value $A_{corr}$ using $\Delta S$. In this way, the percent bias may be linked through $\Delta S$ into Equation 7. The percent bias values may be pulled toward the center of a bias distribution through the linkage of $\Delta S$ to the percent bias. As $\Delta S$ is responsive to bias, changing $\Delta S$ affects the amount of bias remaining in the compensated analyte concentration of the sample.

The responsiveness of $\Delta S$ to one or more errors in the analysis may be represented by a predictor function. To determine one or more predictor functions, the deviation in the slope of the correlation equation in response to the one or more errors ($\Delta S_{cal}$) may be determined from experimental data, such as during factory calibration, as follows:

$$\Delta S_{cal} = \frac{i - Int}{A_{ref}} - S_{cal}, \quad \text{(Equation 9)}$$

where i is a value of the output signal from a biosensor system, Int is the intercept from a reference correlation equation, $A_{ref}$ is the reference analyte concentration of the sample, such as obtained from a reference instrument, and $S_{cal}$ is the slope from a reference correlation equation, such as $i=S_{cal}*A_{ref}+Int$. One or more $\Delta S_{cal}$ values may be determined at each reference analyte concentration. In this manner, for multiple known analyte concentrations, an output signal value may be obtained from the biosensor system and a corresponding $\Delta S_{cal}$ value determined. An initial predictor function may be determined by taking the $\Delta S_{cal}$ values from Equation 9 and correlating them to an error parameter.

Predictor functions compensate the measured analyte concentration for one or more errors in the analyte concentration analysis. One or more predictor functions may be used. A predictor function that perfectly correlates with the total slope deviation $\Delta S$ would provide an ultimate total error compensation of the analyte concentration. Such a hypothetical, perfectly correlated predictor function could be used to compensate for all errors in the analysis without having to know the exact cause of the total slope deviation $\Delta S$, and thus the bias of the measured analyte concentration. Predictor functions include at least one index function, and one or more of the index functions may be complex. Preferably, predictor functions include at least one complex index function.

An index function is responsive to at least one error parameter. An index function may be a calculated number that correlates with an error parameter, such as hematocrit or temperature, and represents the influence of this error parameter on the slope deviation $\Delta S$. Thus, error parameters may be any value responsive to one or more errors in the output signal. Index functions may be experimentally determined as a regression equation of the plot between $\Delta S_{cal}$ and an error parameter.

Index functions may be determined using error parameters values from the analysis of the analyte, such as the intermediate signals from an output signal, or from sources independent of the analyte output signal, such as thermocouples, additional electrodes, and the like. Thus, the error parameters may be extracted directly or indirectly from the output signal of the analysis and/or obtained independently from the output signal. Any error parameter may be used to form the terms, such as those described in Intl. Pub. No. WO 2009/108239, filed Dec. 6, 2008, entitled "Slope-Based Compensation," and the like.

Temperature may be considered an error parameter because an error in concentration values may arise from performing an analysis at a temperature other than that at which the reference correlation was determined. For example, temperature affects the oxidation and diffusion of glucose in a sample of whole blood and the diffusion of optically active molecules. The temperature for the analysis may be determined from any source, such as a thermocouple, calculated estimates, and the like. Thus, $f(Index)_{Temp}$ relates temperature to the deviation in slope between the reference correlation slope determined at a reference temperature and the hypothetical slope of the line that would provide the temperature affected analyte concentration at the temperature at which the analysis was performed. The index function for temperature $f(Index)_{Temp}$ may be stored in the biosensor system with the reference correlation equation.

Figure 4:
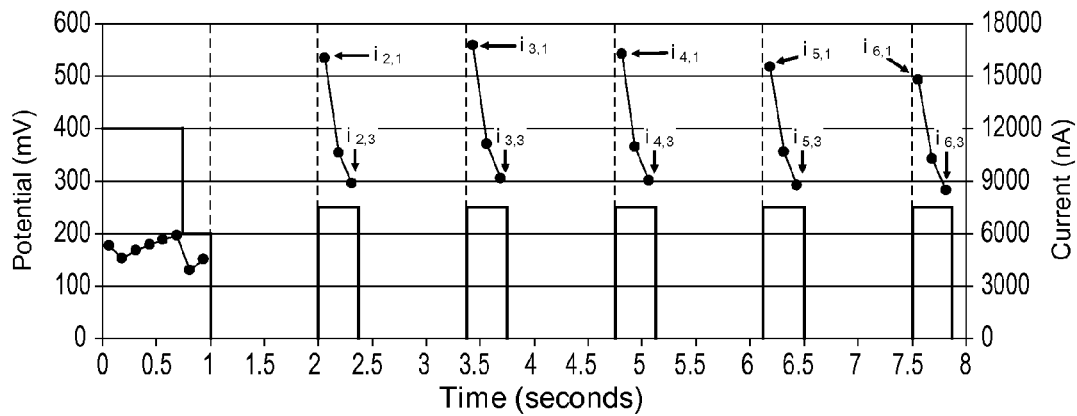
FIG. 4 depicts a gated pulse sequence where the input signal includes multiple pulses.

FIG. 4 depicts a gated pulse sequence where the input signal includes multiple pulses. The output signal current values resulting from the pulses are depicted above each pulse. The recorded intermediate signal current values are depicted as circles. Each of the i values is a current value of the output signal responsive to the input signal. The first number in the subscript of the i values denotes the pulse number, while the second number in the subscript denotes the order of the output signal as the current values were recorded. For example, $i_{2,3}$ denotes the third current value recorded for the second pulse.

As previously discussed, index functions may include ratios extracted from the intermediate output signals as depicted in FIG. 4. For example, the intermediate signal values may be compared within an individual pulse-signal decay cycle, such as ratios $R3=i_{3,3}/i_{3,1}$, $R4=i_{4,3}/i_{4,1}$, and the like. In another example, the intermediate signal values may be compared between separate pulse-signal decay cycles, such as ratios $R3/2=i_{3,3}/i_{2,3}$, $R4/3=i_{4,3}/i_{3,3}$, and the like.

Index functions also may include combinations of ratios extracted from the output signal depicted in FIG. 4. In one example, an index function may include a ratio of ratios, such as Ratio3/2=R3/R2, Ratio4/3=R4/R3, and the like. In another example, an index function may include a combination of indices. For example, a combination index, Index-1, may be represented as Index-1=R4/3−Ratio3/2. In another example, a combination index Index-2 may be represented as Index-2= $(R4/3)^p$−$(Ratio3/2)^q$, where p and q independently are positive numbers.

An index function is complex when the function includes a combination of terms modified by weighing coefficients. The combination is preferably a linear combination, but other combination methods may be used that provide weighing coefficients for the terms. Each term may include one or more error parameters. An example of a complex index function is represented as follows:

$$f(CIndex) = a_1 + (a_2)(R3/2) + \quad \text{(Equation 10)}$$
$$(a_3)(R4/3) + (a_4)(R5/4) + (a_5)(R3/2)(G_{raw}) +$$
$$(a_6)(R4/3)(G_{raw}) + (a_7)(R3/2)(Temp) +$$
$$(a_8)(R4/3)(Temp) + (a_9)(Temp) + (a_{10})(G_{raw}) + \ldots ,$$

where $a_1$ is a constant, $a_2$-$a_{10}$ independently are weighing coefficients, $G_{raw}$ is the determined analyte concentration of the sample without compensation, and Temp is temperature. Each of the weighing coefficients ($a_2$-$a_{10}$) is followed by its associated term.

There are at least three basic types of terms in the complex index function represented by Equation 10: (1) the individual ratio indices extracted from the output signal, such as R3/2 and R4/3, (2) the interaction terms between the ratio indices extracted from the output signal and the temperature or $G_{raw}$, such as $(R3/2)(G_{raw})$ and (R3/2)(Temp), and (3) temperature and $G_{raw}$. The terms may include values other than error parameters, including $G_{raw}$. Other terms also may be used, including, but not limited to a combination index function, as previously described. The complex index function may be solved to provide a complex index value when the terms are replaced with the appropriate values. Statistical processing may be performed on the multiple terms to determine one or more constants and weighing coefficients. Statistical package software, including MINITAB (MINTAB, INC., State College, Pa.), may be used to perform the statistical processing.

The constant $a_1$ may be determined by regression or other mathematical technique. While a single constant is shown in Equation 10, a constant is not required; more than one may be used, and may be equal to 0. Thus, one or more constants may or may not be included in the complex index function. One or more constants also may be combined with an index function in forming the predictor function, such as the $b_0$ constant previously described in relation to Equation 8, for example.

While terms having weighing coefficients of one may be used, a complex index function includes at least two terms that are modified by weighing coefficients. Weighing coefficients are numerical values other than one or zero. Preferably, each term including an error parameter is modified by a weighing coefficient. More preferably, each non-constant term of the complex index function is modified by a weighing coefficient. Weighing coefficients may have positive or negative values. Weighing coefficients may be determined through the statistical processing of the experimental data collected from a combination of multiple analyte concentrations, different hematocrit levels, different temperatures, and the like.

Table 1, below, lists the weighing coefficients and p-values resulting from a multi-variable regression of data taken from glucose output signals (currents) from capillary and venous blood samples at 21° C. and 18° C. of a donor study with 52 donors. Each blood sample from each donor was analyzed twice for glucose, to give approximately 104 data points in the data population. The samples were analyzed using a gated amperometric input signal where selected intermediate output signals were recorded from the pulses. MINITAB version 14 software was used with the Multi-Variant Regression of Linear Combinations of Multiple Variables option chosen to perform the multi-variable regression. Other statistical analysis or regression options may be used to determine the weighing coefficients for the terms.

TABLE 1

Results of multivariable regression.

| Term | Weighing Coefficient | Coefficient Standard Error | T | P |
|---|---|---|---|---|
| Constant | 133.52 | 48.35 | 2.76 | 0.006 |
| R3/2 | 204.96 | 71.03 | 2.89 | 0.004 |
| R4/3 | −356.79 | 96.47 | −3.70 | 0.000 |
| (R3/2)($G_{raw}$) | −0.0408 | 0.1163 | −0.35 | 0.726 |
| (R4/3)($G_{raw}$) | −0.0338 | 0.1812 | −0.19 | 0.852 |
| (Temp)(R3/2) | −12.237 | 3.704 | −3.30 | 0.001 |
| (Temp)(R4/3) | 15.565 | 5.115 | 3.04 | 0.002 |
| Temp | −2.516 | 2.503 | −1.01 | 0.315 |
| $G_{raw}$ | 0.08274 | 0.09661 | 0.86 | 0.392 |

The resulting complex index function may be represented as follows:

$$\Delta S_{RegA} = 134 + (205)(R3/2) - \quad \text{(Equation 11)}$$
$$(357)(R4/3) - (0.041)(R3/2)(G_{raw}) -$$
$$(0.034)(R4/3)(G_{raw}) - (12.2)(Temp)(R3/2) +$$
$$(15.6)(Temp)(R4/3) - (2.52)(Temp) + (0.0827)(G_{raw}),$$

where $\Delta S_{RegA}$ is a complex index function describing $\Delta S_{cal}$, defined as $\Delta S_{cal}=(i/A_{ref})-S_{cal}$, where $A_{ref}$ is the reference analyte concentration value obtained from the YSI reference instrument and $S_{cal}$ is the slope from the reference correlation equation, as previously discussed with regard to Equation 7, for example. The $R^2$ value reflecting how well the outputs from the $\Delta S_{RegA}$ complex index function correspond to the $\Delta S_{cal}$ values was 77.2% ($R^2$*100%). Thus, the $R^2$ value indicated the correlation between the complex index function and $S_{cal}$. Larger $R^2$ values reflect the complex index being better at describing $\Delta S_{cal}$.

Figure 1B:
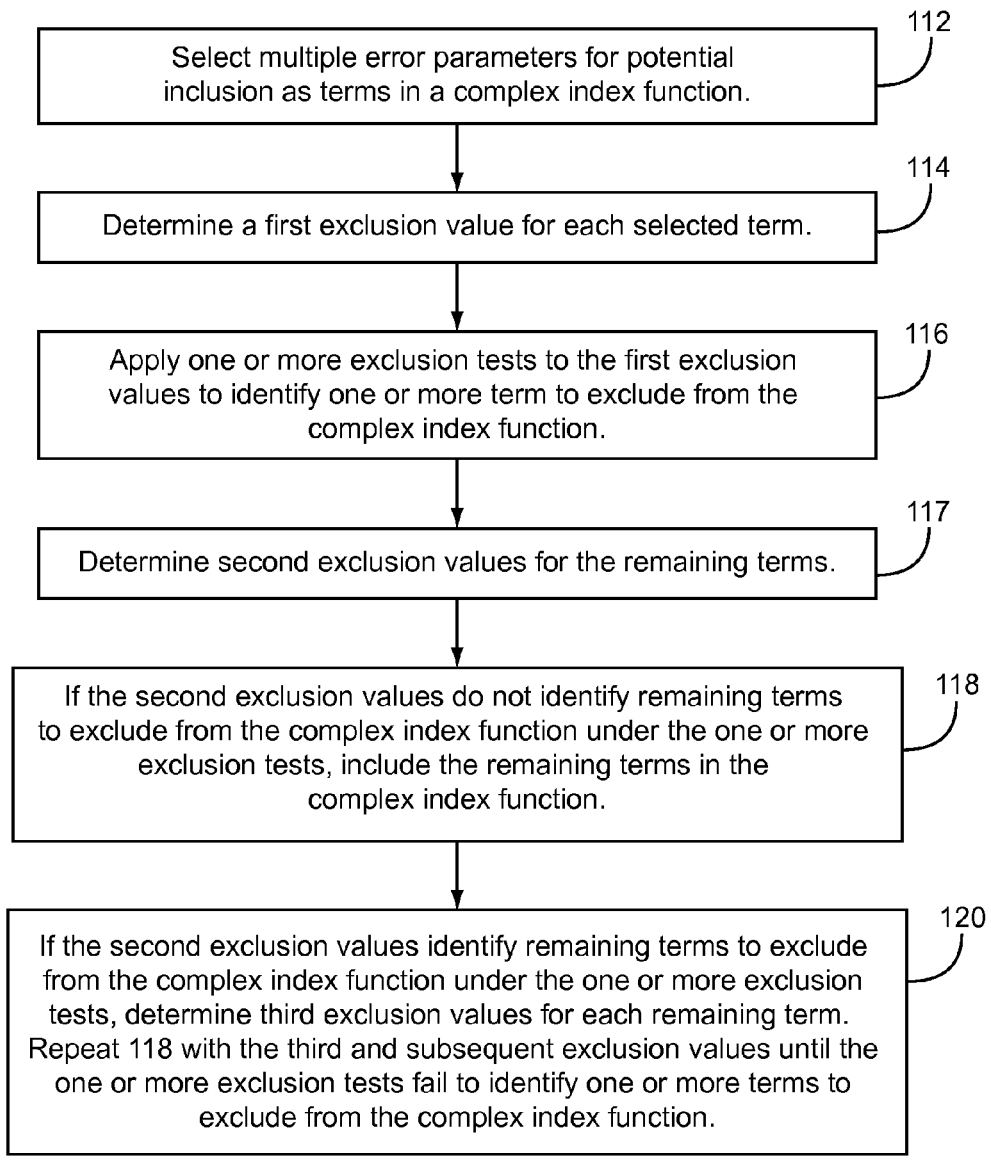
FIG. 1B represents a method for selecting terms for inclusion in a complex index function.

FIG. 1B represents a method for selecting terms for inclusion in a complex index function. In 112, multiple error parameters are selected as terms for potential inclusion in the complex index function. The error parameters may be extracted directly or indirectly from an output signal responsive to a light-identifiable species or from the redox reaction of an analyte in a sample of a biological fluid. The error parameters also may be obtained independently from the output signal, such as from a thermocouple. The terms may include values other than error parameters. In 114, one or more mathematical techniques are used to determine first exclusion values for each selected term. The mathematical techniques may include regression, multi-variant regression, and the like. The exclusion values may be p-values or the like. The mathematical techniques also may provide weighing coefficients, constants, and other values relating to the selected terms.

In 116, one or more exclusion tests are applied to the exclusion values to identify one or more terms to exclude from the complex index function. At least one term is excluded under the test. In 117, the one or more mathematical techniques are repeated to identify second exclusion values for the remaining terms. In 118, if the second exclusion values do not identify remaining terms for exclusion from the complex index function under the one or more exclusion tests, the remaining terms are included in the complex index function. In 120, if the second exclusion values identify remaining terms to exclude from the complex index function under the one or more exclusion tests, the one or more mathematical techniques of 117 may be repeated to identify third exclusion values for the remaining terms. These remaining terms may be included in the complex index function as in 118 or the process may be iteratively repeated as in 120 until the exclusion test fails to identify one or more terms to exclude.

Table 1, above, also lists p-values for each term. The p-values indicate the probability of affecting the correlation between the complex index function and $\Delta S$ if the term were eliminated from the complex index function. For example, a p-value of 0.05 or more for a term means that the probability is 5% or more that the elimination of the term from the complex index function would not reduce the correlation of the complex index function to $\Delta S$. Thus, p-values may be used as exclusion values for an exclusion test to select terms for potential exclusion from the complex index function. The smaller the numerical p-value selected as an exclusion value, the more terms will be excluded from the complex index function.

When the exclusion test uses p-values as exclusion values, exclusion p-values from about 0.01 to about 0.10 are preferred, with exclusion p-values values from about 0.03 to about 0.07 being more preferred. In addition to exclusion tests based on p-values, other exclusion tests also may be used to identify potential terms for exclusion from the complex index functions. Removing terms from the complex index function that do not affect the correlation between the complex index function and $\Delta S$ in an undesirable way, allows the desired correlation between the complex index function and $\Delta S$. Thus, the desired improvement in measurement performance may be achieved by the compensation equation, while providing a shorter analysis time. Furthermore, the precision of subsequent analyses performed using different biosensor systems and conditions may be improved through the removal of undesirable terms from the complex index function.

With regard to the terms in Table 1, terms having p-values greater than 0.05 were selected for potential removal from the complex index function. Thus, the terms $(R3/2)(G_{raw})$, $(R4/3)(G_{raw})$, Temp and $G_{raw}$ were identified as terms that may be appropriate for removal from the complex index function after the first multivariable regression. As the $(R4/3)(G_{raw})$ term showed the greatest p-value (0.852), the term was removed and the multivariable regression was repeated. This and a third iteration of the multivariable regression identified that the Temp and $G_{raw}$ terms had the second and third highest p-values. With the removal of the $(R4/3)(G_{raw})$, Temp, and $G_{raw}$ terms, it was unexpectedly determined that the p-value of the $(R3/2)(G_{raw})$ term had fallen under the 0.05 exclusion value, as shown in Table 2, below. Thus, while the weighing coefficient for the $(R3/2)(G_{raw})$ term is numerically small (0.00799) in relation to the other weighing coefficients, the term contributed to the complex index function's ability to correlate with $\Delta S$. Preferably, an iterative process of selecting and eliminating terms with the largest undesirable departure from an exclusion test is repeated until the remaining terms meet the test.

TABLE 2

Results of multivariable regression with the reduced term set.

| Term | Weighing Coefficient | Coefficient Standard Error | T | P |
|---|---|---|---|---|
| Constant | 95.463 | 3.930 | 24.29 | 0.000 |
| R3/2 | 177.66 | 68.22 | 2.60 | 0.010 |
| R4/3 | −289.31 | 70.91 | −4.08 | 0.000 |
| $(R3/2)(G_{raw})$ | $7.9899 \times 10^{-3}$ | $7.575 \times 10^{-4}$ | 10.55 | 0.000 |
| (Temp)(R3/2) | −11.221 | 3.550 | −3.16 | 0.002 |
| (Temp)(R4/3) | 11.928 | 3.709 | 3.22 | 0.001 |

The complex index function of Equation 11 after removal of the $(R4/3)(G_{raw})$, Temp, and $G_{raw}$ terms may be represented as follows:

$$\Delta S_{RegB}=95.5+(178)(R3/2)-(289)(R4/3)+(0.00799)(R3/2)(G_{raw})-(11.2)(\text{Temp})(R3/2)+(11.9)(\text{Temp})(R4/3) \quad \text{(Equation 12)}.$$

The $R^2$ value reflecting how well the outputs from the $\Delta S_{RegB}$ equation correspond to the $S_{cal}$ values was 77.1%. Removal of the terms eliminated by the exclusion test from Equation 11 did not cause a significant change (0.1) in the ability of the reduced-term complex index function to describe $\Delta S$. Thus, the ability of the complex index of Equation 12 to describe the errors in the Table 1 data was preserved, while providing a beneficial reduction in the number of terms in relation to Equation 11.

Figure 5A:
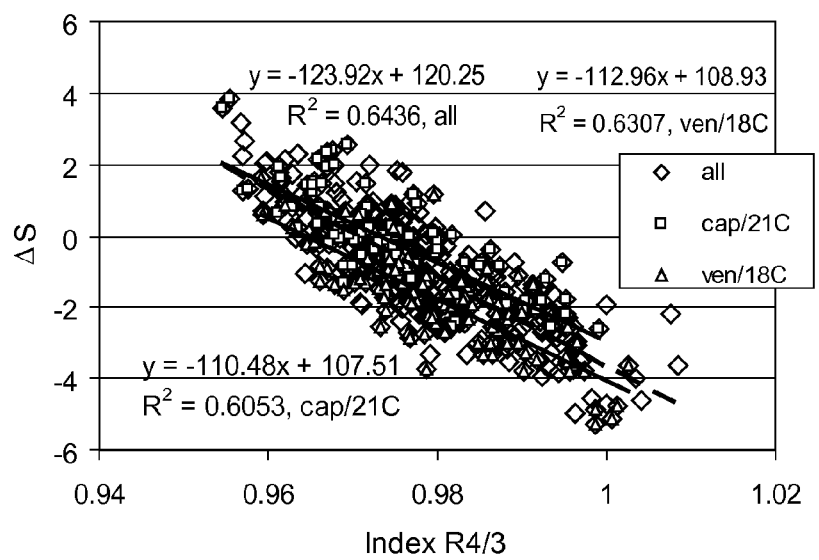
FIG. 5A depicts a graph of the correlations between $\Delta S$ and R4/3 index values.
Figure 5B:
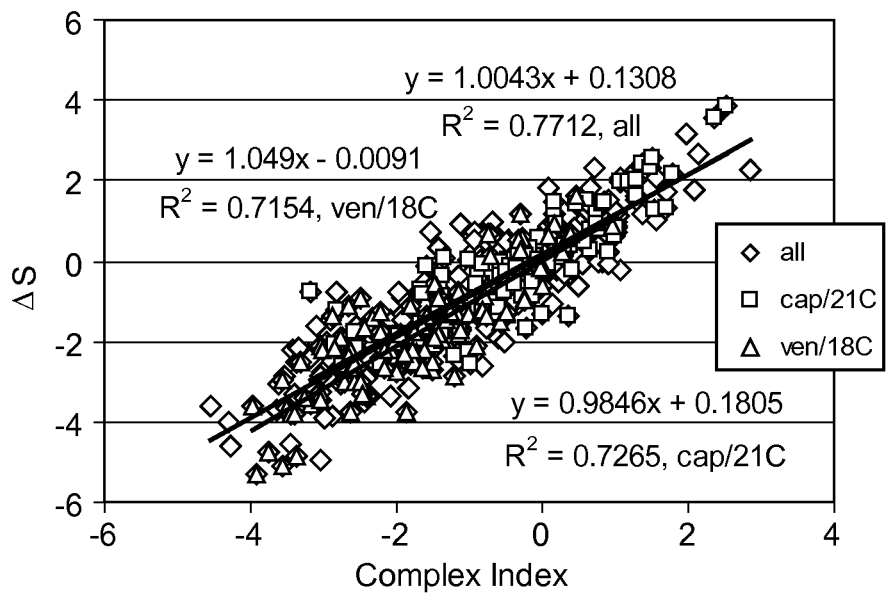
FIG. 5B depicts a graph of the correlations of $\Delta S$ with complex index values.

FIG. 5A is a graph for the data from the donor study previously discussed with regard to Table 1 of the correlations of $\Delta S$ with R4/3 index values. The "cap/21 C" data set represents correlation data from capillary blood samples at approximately 21° C., the "ven/18 C" data set represents correlation data from venous blood samples at approximately 18° C., and the "all" data set represents the overall correlation data from these two samples, as well as capillary blood samples at approximately 18° C. and venous blood samples at approximately 21° C. FIG. 5B is a similar graph of the correlations of $\Delta S$ for the data of Table 1 as a function of the complex index values obtained from Equation 12. The differences between the overall correlation ("all") and the individual correlations at different temperatures are much smaller for the complex index function of FIG. 5B ($R^2=0.77$) than for the R4/3 ratio index function of FIG. 5A ($R^2=0.64$). Although the approximately 0.13 difference between these $R^2$ values is numerically small, it represents a 13% improvement in the correlation between $\Delta S$ and the complex index function in relation to the R4/3 ratio index function. Consequently, the biosensor may use a single predictor function, represented as Equation 13 below, to compensate for all four cases of capillary and venous blood samples at the 21° C. and 18° C. temperatures.

$$\Delta S=1.0043*\Delta S_{RegB}+0.1308 \quad \text{(Equation 13)}.$$

In Equation 13, $\Delta S_{RegB}$, the complex index function, is as represented in Equation 12 and the 1.0043 and 0.1308 values are $b_1$ and $b_0$ (from the FIG. 5B plot of "all" data), respectively, as previously described with regard to Equation 8, for example.

Using one or more complex index function responsive to ΔS may reduce the bias spread, which is measured by the standard deviation of the combined biases. The smaller the standard deviation of the combined biases, the smaller the bias spread, and the more accurate and/or precise the analysis of the analyte in the sample. The effectiveness of the compensation at improving the measurement performance of an analysis is directly related to the correlation between ΔS and one or more index functions, which directly affects the reduction of the standard deviation (SD) of a bias population. The correlation between ΔS and one or more index or predictor functions may be measured by the correlation coefficient $R^2$. Therefore, the higher the $R^2$ value the better the correlation between ΔS and one or more index or predictor functions, the larger the reduction of the SD value for the combined biases, and the smaller the bias spread after compensation. Preferable complex index functions have an $R^2$ correlation value of about 0.6 and greater with ΔS. More preferable complex index functions have an $R^2$ correlation value of about 0.7 and greater with ΔS. Preferable index or predictor functions provide SD values of less than 5 for the combined biases of a data population. Preferable predictor functions including complex index functions provide SD values of less than 4 for the combined biases of a data population, and more preferably SD values of less than 3 for the combined biases of the data population.

The empirical relationship between standard deviation and bias spread is observed in Table 3, below. The mean of the combined biases, the SD of the combined biases, and the percent of the concentration analysis (data population) falling within a ±10% combined bias limit before and after R4/3+Temp index and complex index compensation are listed for the capillary blood samples previously described with regard to Table 1 and analyzed for glucose at 21° C. and 18° C. The "R4/3+Temp" abbreviation is used to describe compensation with a R4/3 index function and with a temperature index function, as further discussed with regard to Table 4.

TABLE 3

Compensation results using R4/3 + Temp and complex indices.

| Temperature | Measurement Performance | Before compensation ($G_{raw}$) | R4/3 + Temp index compensation | Complex index compensation |
|---|---|---|---|---|
| 21° C. | Mean bias/%-bias | −1.03 | 0.0072 | 0.329 |
| | SD of bias/%-bias | 6.315 | 4.23 | 3.7 |
| | % ±10% | 84.9 | 98.1 | 99.1 |
| 18° C. | Mean bias/%-bias | −9.29 | −2.44 | −1.22 |
| | SD of bias/%-bias | 6.91 | 4.71 | 4.18 |
| | % ±10% | 55.2 | 94.7 | 98.1 |

The mean of the combined biases as calculated from the determined analyte concentrations without compensation ($G_{raw}$) showed that both the 18° C. and the 21° C. data populations were negatively offset in relation to zero bias. At 21° C., the mean of −1.03 for the combined biases is believed to be within the error of the biosensor system. However, at 18° C., the mean of −9.29 for the combined biases is believed attributable to temperature error. For the lower temperature 18° C. data, the significantly higher numerical value of nine indicated that the uncompensated data from the system was centered at the lower boundary of a ±10 combined bias limit, significantly away from the center of zero bias. Thus, about half of the data population was outside the boundary of a ±10 combined bias limit.

For the 21° C. data set, R4/3+Temp index function compensation provided a reduction of greater than two units (6.315−4.23=2.085) in standard deviation. This greater than two unit reduction is significant, as on average, a standard deviation of 5 units or less will place about 95% of the data within a ±10% combined bias limit and about 63% of the data within a ±5% combined bias limit. Thus, the R4/3+Temp index function compensation brought about 98% of the 21° C. data within the boundary of a ±10% combined bias limit and about 77% of the data within the boundary of a ±5% combined bias limit.

In relation to R4/3+Temp index function compensation, complex index function compensation reduced standard deviation by approximately an additional 0.5 units. Thus, the complex index compensation brought about 99% of the data within the boundary of a ±10% combined bias limit and about 88% of the data within the boundary of a ±5% combined bias limit. While the improvement for complex index compensation in relation to R4/3+Temp index function compensation is not as great for this data as observed for R4/3+Temp index function compensation in relation to no compensation, the resistance of the system to perturbation when the data set is less centered (larger mean of the combined biases) is significantly increased.

Perturbation resistance may be thought of as how well a system provides accurate and/or precise analyte concentration values when errors are present in the analysis. Perturbation resistance is determined by subtracting twice the standard deviation from 10 to provide a perturbation resistance indicator (PRI). For the 21° C. data population in Table 3, the PRI is 1.54 (10−2*4.23) for the R4/3+Temp index function compensation and 2.6 (10−2*3.7) for the complex index function compensation. As the uncompensated 21° C. data is substantially centered with a numerical mean of one, the approximately 68% increase in the PRI provided by the complex index function compensation in relation to the R4/3+Temp index function compensation moves one additional percent of the data within the boundary of a ±10% combined bias limit.

However, when the system is perturbed by an error causing a spread in the uncorrected data, as was observed as a numerical increase in the mean of the combined biases for the 18° C. data, the benefit provided by complex index function compensation significantly increased. For the perturbed 18° C. data, the standard deviation was reduced by 2.2 units through R4/3+Temp index function compensation and was further reduced by approximately 0.5 unit through complex index function compensation. Thus, complex index function compensation provided an approximately 0.5 unit SD reduction in standard deviation at both temperatures in relation to R4/3+Temp index function compensation. This translates into complex index function compensation having an enhanced ability to bring high bias data into an acceptable range in relation to compensation by the R4/3+Temp index function.

When the PRI values were determined for the 18° C. data, R4/3+Temp index function compensation provided a value of 0.58, while complex index function compensation provided a value of 1.64, an approximately 180% increase in the PRI for complex over R4/3+Temp index function compensation. While the 68% increase in the PRI provided by complex index function compensation moved an additional 1% of the closely grouped 21° C. data within the boundary limit of a ±10% combined bias limit, the 180% increase in the PRI provided by complex index function compensation moved over three times as much (3.4%) of the numerically higher mean 18° C. data within the boundary limit of a ±10% combined bias limit. Thus, the greater the error in the uncompensated data, the better complex index function compensation performed at reducing bias to within the boundary of a ±10% combined bias limit.

Complex index function compensation provided an approximately 17% (99.1−84.9/84.9*100%) increase in the percentage of data points within the boundary of a ±10% combined bias limit in relation to the uncompensated data from a R4/3+Temp index function compensation and from a complex index function compensation including temperature in the terms. The percent of the data from the donor study previously discussed with regard to Table 1 falling within ±10%, ±8%, and ±5% combined bias limits was determined in addition to the standard deviation (SD) for the combined biases of the data population. The samples were analyzed using a gated amperometric input signal where selected intermediate output signals were recorded from the pulses.

TABLE 4

| | Compensation with R4/3 + Temp and Complex Index Functions | | | | | | | | | | |
|---|---|---|---|---|---|---|---|---|---|---|---|
| | Un-comp | R4/3 + Temp index functions | | | | | Complex index function including T | | | | |
| | Cap/21 C. | Cap/21 C. | Ven/22 C. | Cap/18 C. | Ven/18 C. | all | Cap/21 C. | Ven/22 C. | Cap/18 C. | Ven/18 C. | all |
| % in ±10% | 84.9 | 98.1 | 96.2 | 96.2 | 94.3 | 96.2 | 99.1 | 99.0 | 97.2 | 98.1 | 98.3 |
| % in ±8% | | 93.4 | 94.3 | 85.8 | 91.5 | 91.3 | 96.2 | 98.1 | 91.5 | 93.4 | 94.7 |
| % in ±5% | | 77.4 | 84.0 | 66.0 | 62.3 | 72.3 | 87.7 | 87.6 | 76.4 | 78.3 | 82.5 |
| SD %-bias | | 4.23 | 4.01 | 5.23 | 4.72 | | 3.62 | 3.47 | 4.57 | 4.13 | | points at the higher 21° C. temperature and an approximately 78% (98.1−55.2/55.2*100%) increase in the percentage of data points within the boundary of a ±10% combined bias limit in relation to the uncompensated data points at the lower 18° C. temperature. While the difference between the R4/3+Temp index function and the complex index function corrections was not as large for this substantially centered uncorrected data, the improvement provided by complex index function correction is significant as fewer analyses would be outside of the boundary of a ±10% combined bias limit. By reducing the number of readings outside of the bias limit, more of the readings obtained could be used for accurate therapy by a patient when blood glucose is being monitored, for example. Additionally, the need to discard and repeat the analysis by the patient also may be reduced.

Figure 6A:
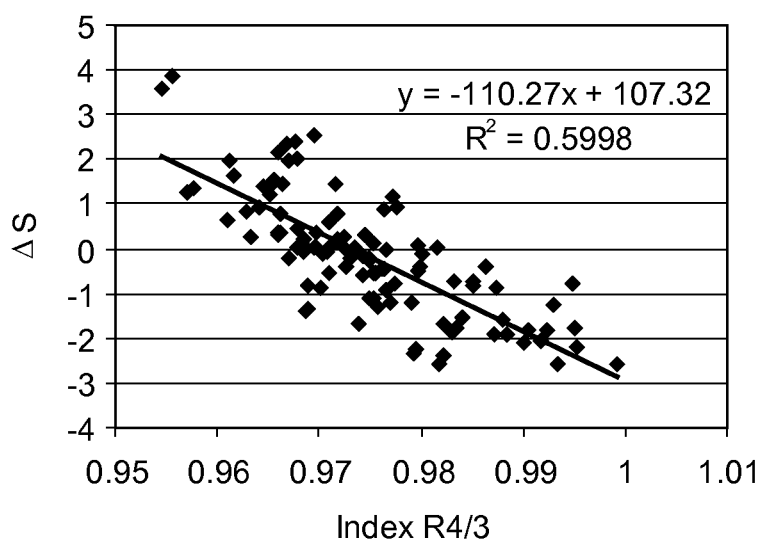
FIG. 6A depicts a graph of the correlations of $\Delta S$ for blood samples at 21° C. with R4/3 index values.
Figure 6B:
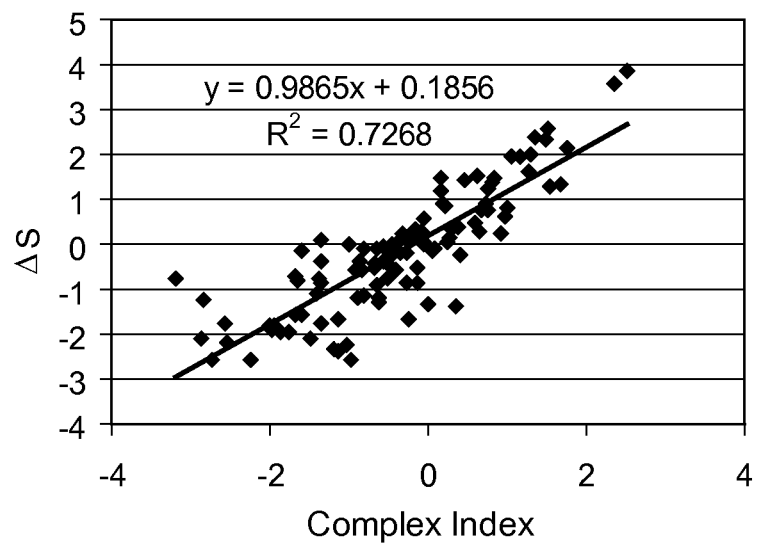
FIG. 6B depicts a graph of the correlations of $\Delta S$ for blood samples at 21° C. with complex index values.
Figure 6C:
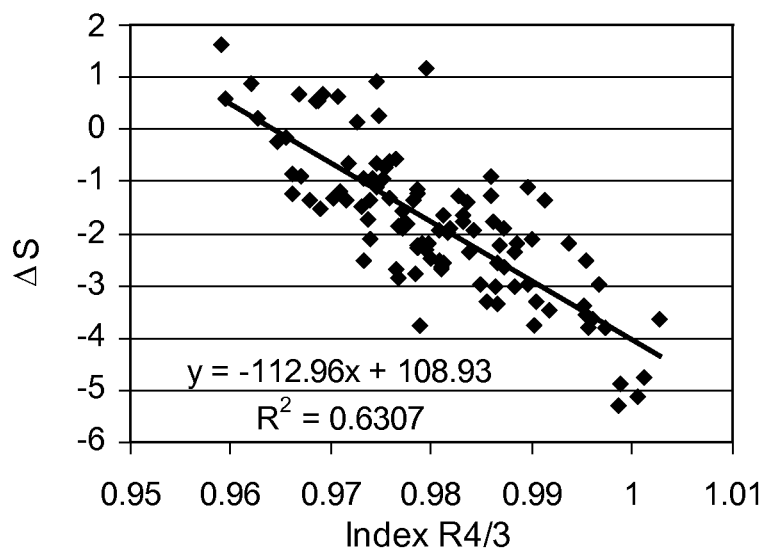
FIG. 6C depicts a graph of the correlations of $\Delta S$ for blood samples at 18° C. with R4/3 index values.
Figure 6D:
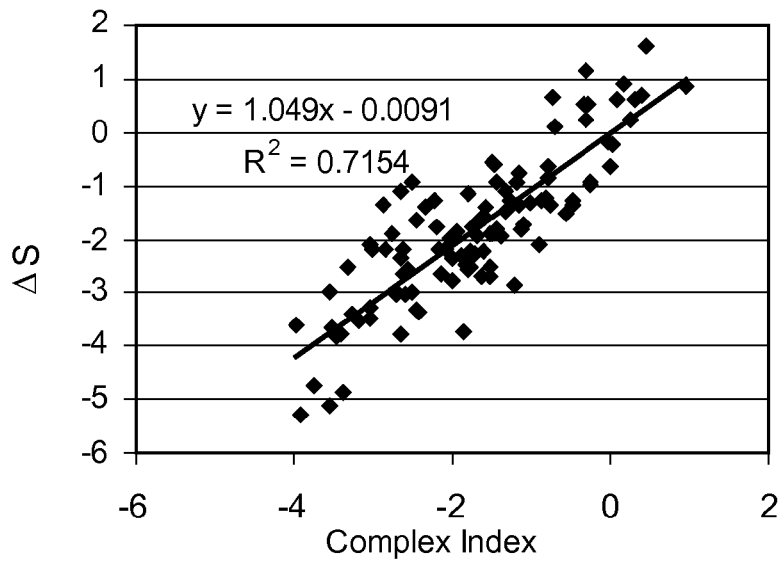
FIG. 6D depicts a graph of the correlations of $\Delta S$ for blood samples at 18° C. with complex index values.

FIG. 6A is a graph of the capillary and venous blood samples previously discussed in relation to Table 1 at 21° C. for the correlations of ΔS with the R4/3 index values. FIG. 6B is a graph of the correlations of ΔS for the same data with the complex index values of Equation 12. The $R^2$ values for these graphs were 0.5998 and 0.7268, respectively, indicating an approximately 21% (0.7269−0.5998/0.5998) improvement in the correlation of the complex index function to ΔS in relation to the correlation of the R4/3 index function to ΔS. Similarly, FIG. 6C and FIG. 6D plot the correlations to ΔS for capillary and venous blood samples at 18° C. with the R4/3 index values (FIG. 6C), and with the complex index values from Equation 12 (FIG. 6D). Comparison of the $R^2$ values for the R4/3 and complex index functions (0.6307 and 0.7154, respectively) shows an approximately 13.5% (0.7154−0.6307/0.6307) improvement in the correlation of the complex index function to ΔS in relation to the correlation of the R4/3 index function to ΔS.

The slope deviation, ΔS, and/or related complex index functions may be normalized to represent the %-bias in the correlation of analyte concentrations with output signals. In normalization, the slope deviation, index or complex index function, or other parameter is adjusted (multiplied, divided, or the like) by a variable to reduce the statistical effect of changes in the parameter, improve the differentiation in variations of the parameter, standardize measurements of the parameter, a combination thereof, or the like.

Table 4, below, compares determined raw glucose concentrations with compensated glucose concentrations resulting R4/3+Temp index function compensation was performed with the predictor function $f(predictor)=a_1*R4/3+a_0$, determined by comparing $\Delta S_{cal}$ (observed from the recorded current values) with R4/3, where $a_1$ and $a_0$ represent a slope and intercept, respectively. The temperature sensitivity $\Delta S_T$ of the data also was determined using the relationship:

$$\Delta S_T = f(Index)_{Temp} = c_1 * T + c_0 \quad \text{(Equation 14)},$$

where $f(Index)_{Temp}$ is as previously described, T is temperature, and $c_1$ and $c_0$ represent a slope and intercept, respectively.

The corrected glucose concentration was then determined using the relationship:

$$G_{corr} = (i - Int)/(S_{cal} + \Delta S_T + f(predictor)) \quad \text{(Equation 15)},$$

where i is a value of the output signal from a biosensor system, Int is the intercept from a reference correlation equation, and $G_{corr}$ is the corrected glucose concentration of the sample.

The percentage of the data points (corrected glucose sample concentrations) falling within the boundary of a ±10%, ±8%, or ±5% combined bias limit was determined through the relationship $G_{corr} - G_{ref}$ if $G_{ref}$ was less than 75 mg of glucose per deciliter (mg/dl) of sample, where $G_{ref}$ is the reference glucose concentration of the sample as determined by a YSI reference instrument. The relationship 100%*$(G_{corr} - G_{ref})/G_{ref}$ was used to determine the percentage of the corrected glucose sample concentrations falling within the boundary limits when the data point was greater than or equal to 75 mg/dl.

Complex index function compensation was performed with error parameters determined from the intermediate currents from the samples, temperature values, and $G_{raw}$ by selecting terms, constants, and weighing coefficients as previously described. p-values were used to perform the exclusion test for the terms to include in the complex index function f(CIndex). $\Delta S_{cal}$ was then compared with the f(CIndex) to obtain $\Delta S_{cal} = b_1 * f(CIndex) + b_0$, where $b_1$ and $b_0$ represent slope and intercept, respectively. When $b_1$ is approximately one and/or $b_0$ is approximately zero, the f(CIndex) may approximate ΔS without one or both of these modifications. The percentage of the data points (corrected glucose concentrations of each sample) falling within the boundary of a ±10%, ±8%, or ±5% combined bias limit was determined as previously for the R4/3+Temp index function compensation.

When the percentage of analyte concentrations falling within the boundary of the narrowest ±5% combined bias limit are considered, R4/3+Temp index function compensation placed approximately 72% of "all" the samples within the boundary, while complex index function compensation placed approximately 82% of the samples within the boundary. This represents an approximately 14% (82−72/72*100) increase in the total number of corrected analyte concentration values falling within the narrowest ±5% combined bias limit. This significant increase in measurement performance provided by the complex index function compensation in relation to the R4/3+Temp index function compensation was observed even though both methods included a compensation for the temperature differences. Thus, at a measurement performance cut-off of a ±5% combined bias limit, a patient would have to discard and repeat approximately 14% fewer analysis from a glucose biosensor system using complex index function compensation than from the same glucose biosensor system using R4/3+Temp index function compensation. The same glucose biosensor system lacking compensation would require approximately 56% of the glucose analyses to be discarded at the ±5% combined bias limit, rendering the uncompensated system effectively useless for achieving the measurement performance cut-off of a ±5% combined bias limit. A significant decrease (~0.6 units on average) in the standard deviation of the bias for each of the four individual data populations between the R4/3+Temp and complex index function compensations was observed.

Figure 6E:
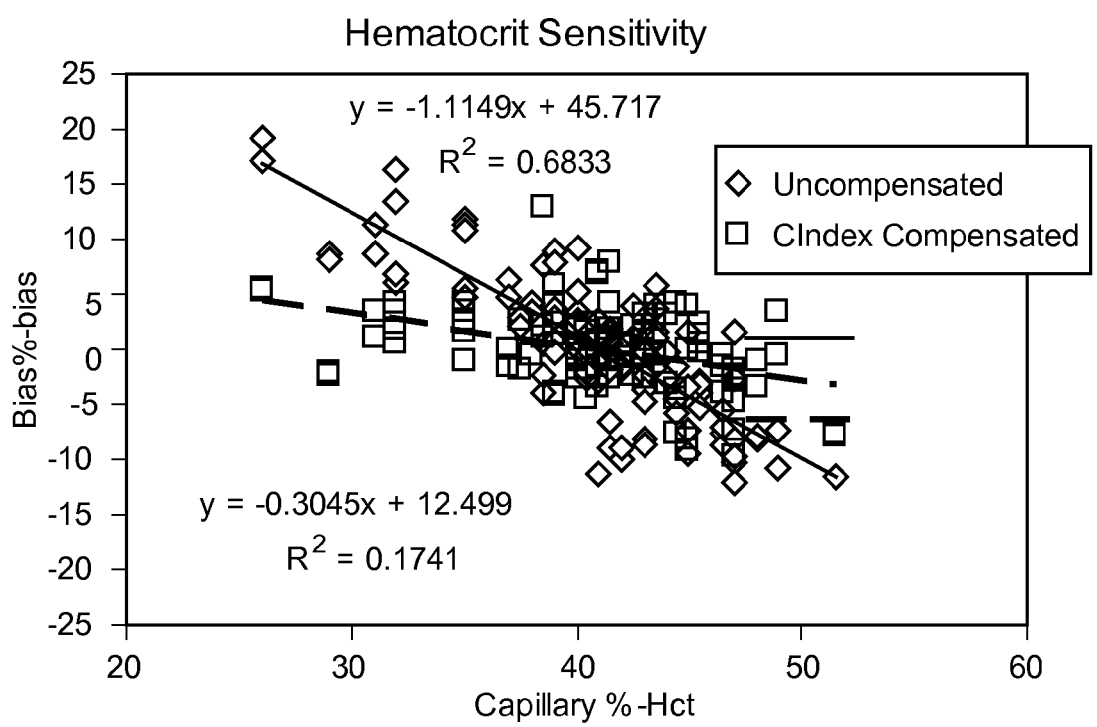
FIG. 6E depicts a graph of hematocrit sensitivity in combined bias vs. % Hct.

FIG. 6E depicts a graph of hematocrit sensitivity in combined bias vs. % Hct. In relation to the uncompensated determined glucose concentrations, the complex index function compensation reduced hematocrit sensitivity from about −1.11 (bias/% bias)/% Hct to about −0.3 (bias/% bias)/% Hct, an approximately 70% reduction. Thus, complex index function compensation substantially reduced the susceptibility of the analysis system to reductions in measurement performance from hematocrit bias.

In addition to $\Delta S$, an index function may represent $\Delta S/S$, a normalized form of slope deviation. Thus, $\Delta S/S$ may be substituted for $\Delta S$. Normalization may be achieved through the relationships $\Delta S/S_{cal}$ or $S/S_{cal}$, for example. As such, the slope deviation, $\Delta S$, in Equation 7 may be normalized by the slope of the reference correlation equation, $S_{cal}$, resulting in a compensation correlation between $\Delta S/S_{cal}$ and the index function.

In Equation 7, $\Delta S$ is divided by $S_{cal}$ as follows:

$$A_{corr} = \frac{i - Int}{S_{cal} + \Delta S} = \frac{i - Int}{S_{cal}(1 + \Delta S / S_{cal})}. \quad \text{(Equation 16)}$$

$\Delta S/S_{cal}$ may be substituted with a predictor function, f(predictor), which may include a complex index function, and may be represented as follows:

$$\Delta S/S_{cal} = f(\text{predictor}) = c_1 * f(\text{CIndex}) + c_0 \quad \text{(Equation 17)}.$$

The predictor function, f(predictor), of Equation 17 may be substituted into Equation 16 as follows:

$$A_{corr} = \frac{i - Int}{S_{cal}(1 + f(\text{predictor}))} = \frac{i - Int}{S_{cal}(1 + (c_1 * f(\text{CIndex}) + c_0))}. \quad \text{(Equation 18)}$$

Solving for the slope deviation, $\Delta S$, provides the following relationship:

$$\Delta S = S_{cal} * f(\text{predictor}) = S_{cal} * (c_1 * f(\text{CIndex}) + c_0) \quad \text{(Equation 19)}.$$

The normalization of the slope deviation, $\Delta S$, by $S_{cal}$ may substantially eliminate the potential effect from different calibrations of $S_{cal}$.

The slope deviation, $\Delta S$, in Equation 7 also may be normalized by multiplication with a normalized slope function, $S_{NML}$, resulting in a compensation correlation between $S_{NML}$ and the complex index function. The normalized slope function $S_{NML}$ may be represented as follows:

$$S_{NML} = S/S_{cal} = \quad \text{(Equation 20)}$$
$$\frac{i - Int}{A_{ref}} * \frac{1}{S_{cal}} = f(\text{predictor}) = d_1 * f(\text{CIndex}) + d_0.$$

Substituting Equation 20 into Equation 7 and replacing $S_{NML}$ with the predictor function, f(predictor), provides the following relationship:

$$A_{corr} = \frac{i - Int}{S_{cal} * S_{NML}} = \quad \text{(Equation 21)}$$
$$\frac{i - Int}{S_{cal} * f(\text{predictor})} = \frac{i - Int}{S_{cal} * (d_1 * f(\text{CIndex}) + d_0)}.$$

Figure 1C:
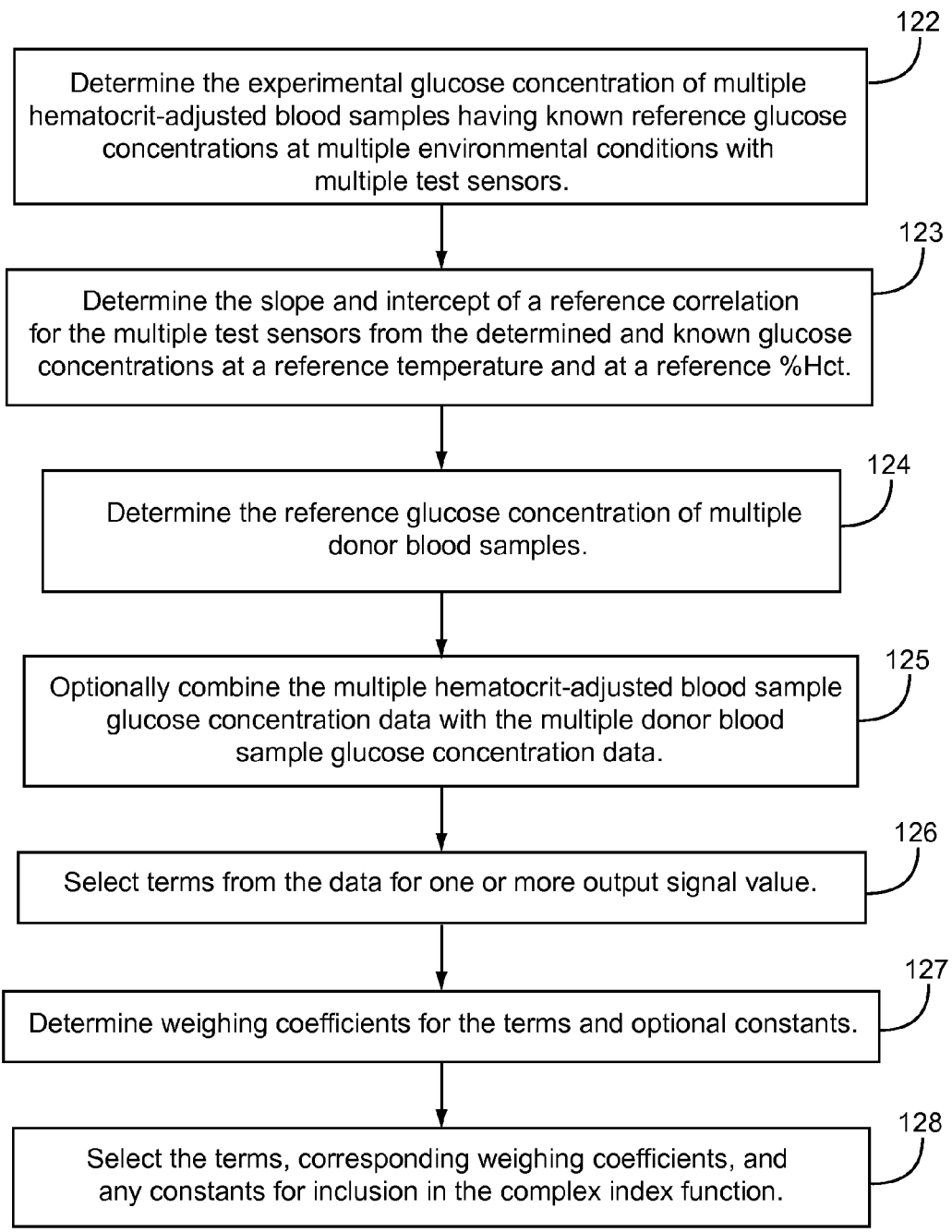
FIG. 1C represents a method of determining a complex index function from hematocrit-adjusted and donor blood samples for use in a measurement device.

FIG. 1C represents a method of determining a complex index function from hematocrit-adjusted and donor blood samples for use in a measurement device. In 122, determine the experimental glucose concentration of multiple hematocrit-adjusted blood samples having known reference glucose concentrations at multiple environmental conditions with multiple test sensors. A reference instrument may be used to determine the known analyte concentrations. In 123, determine the slope and intercept of a reference correlation for the multiple test sensors from the determined and known glucose concentrations at a reference temperature and at a reference % Hct. In 124, determine the reference glucose concentration of multiple donor blood samples. The donor blood samples may have varying glucose concentrations and hematocrit levels. The reference glucose concentration of multiple donor blood samples may be determined at a reference temperature. In 125, optionally combine the multiple hematocrit-adjusted blood sample glucose concentration data with the multiple donor blood sample glucose concentration data. In 126, select terms from the data for one or more output signal value. Terms also may be selected for one or more physical characteristic, environmental condition, concentration value, and the like. In 127, determine weighing coefficients for the terms and optional constants. In 128, select the terms, corresponding weighing coefficients, and any constants for inclusion in the complex index function.

Table 5, below provides determined glucose concentration data for capillary and venous blood samples (about 106 samples) and samples that were spiked with venous blood to adjust the hematocrit content of the samples to about 20 to about 60% Hct (about 60 samples). Thus, hematocrit-adjusted blood samples were prepared as generally described in 122 of FIG. 1C. Unlike the prior analyte concentrations determined from the donor study previously discussed with regard to Table 1, the glucose concentrations of Table 5 were determined using complex index functions derived from different blood samples than the blood samples analyzed for glucose.

Thus, the complex index function implemented by the measurement device to correct bias in Table 5 was previously determined from a different sample population. A p-value exclusion test was used with an exclusion value of 0.05 to select terms for inclusion in the complex index function. After exclusion, the terms remaining in the complex index function were: R4/3, R5/4, R5/4*$G_{raw}$, R/54*Temp, R4/3*Temp, R4/3*R5/4, R4/3*R5/4*$G_{raw}$, R4/3*R5/4*Temp, and Temp. The complex index function included positive or negative weighing coefficients for each term and an initial constant.

A compensation equation was used to determine the corrected glucose concentrations of the blood samples having the general form:

$$G_{corr} = (i - Int)/(S_{cal} * (1 + f(\text{predictor})))$$ (Equation 22), where $f(\text{predictor}) = b_1 * f(\text{CIndex}) + b_0 = \Delta S/S$, the normalized form of slope deviation.

When the predictor function is approximating $\Delta S/S$, the theoretical value of one may be used in place of $b_1$ when $b_1 = 1 \pm 0.2$, preferably one may be used in place of $b_1$ when $b_1 = 1 \pm 0.15$, and more preferably one may be used in place of $b_1$ when $b_1 = 1 \pm 0.1$. When the predictor function is approximating $\Delta S/S$, the theoretical value of zero may be used in place of $b_0$ when $b_0 = 0 \pm 0.03$, preferably zero may be used in place of $b_0$ when $b_0 = 0 \pm 0.02$, and more preferably zero may be used in place of $b_0$ when $b_0 = 0 \pm 0.01$. Other deviation cut-offs may be used to determine when the theoretical values for $b_1$, $b_0$, or both may be used. In addition to substituting $b_1$ and/or $b_0$ with the theoretical values 1 and 0, predetermined values from a look-up table and the like may be substituted based on the same or other deviation cut-offs.

For this data population, $b_1$ was 1.08 and $b_0$ was 0.012. Thus, $b_1$ was estimated at 1, and $b_0$ was estimated at 0. Removing $b_1$ and $b_0$ from the equation provides the relationship as follows:

$$G_{corr} = (i - Int)/(S_{cal} * (1 + f(\text{CIndex})))$$ (Equation 23).

Thus, an output current value responsive to sample glucose concentration was converted into a corrected glucose concentration of the sample using a complex index function representing $\Delta S/S$. Alternatively, a corrected glucose concentration value may be determined from an uncompensated glucose concentration value using a complex index function and an equation having the general form as follows:

$$G_{corr} = G_{raw}/(1 + f(\text{CIndex}))$$ (Equation 24).

TABLE 5

Comparison of f(CIndex) Compensated and Uncompensated Analyses

| Result | Cap/20 C., natural | Cap + spiked | Ven/23 C., natural | Ven + spiked |
|---|---|---|---|---|
| %-within +/−10% after | 99.1 | 97.1 | 98.0 | 96.3 |
| %-within +/−8% after | 97.3 | 95.3 | 95.1 | 93.9 |
| Mean %-bias after | −0.772 | −0.249 | 0.49 | 0.566 |
| SD of %-bias after | 3.61 | 4.63 | 4.39 | 5.0 |
| SD before compensation | 5.35 | 9.3 | 5.99 | 8.9 |
| %-within +/−10% before | 84.5 | 67.8 | 70.6 | 58.3 |

Figure 6F:
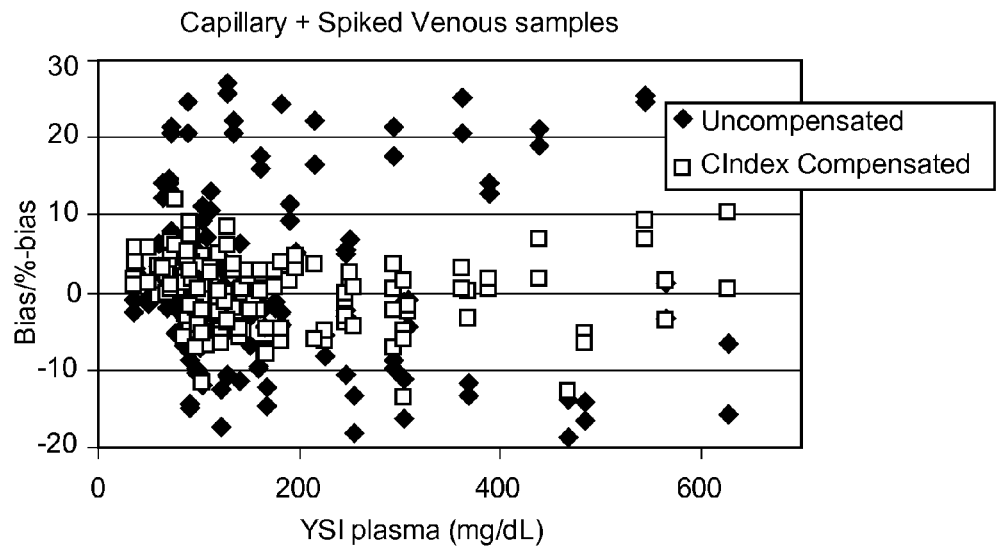
FIG. 6F depicts a graph correlating combined biases to reference glucose concentrations for uncompensated and complex index compensation corrected analyte concentrations.

For the samples including the artificially extended (from 30-50% to about 20-60%) hematocrit range, complex index function correction brought at least 96% of the determined analyte concentrations within the boundary of a ±10% combined bias limit and almost 94% of the determined analyte concentrations within the ±8% combined bias limit. This is a significant improvement in relation to the uncompensated analyses where only about 58% of the spiked venous samples fell within the boundary of the ±10% combined bias limit, a greater than 60% improvement (96−58/58*100). The standard deviation for the combined biases of each of the four data populations also decreased by at least 1.5 units for the corrected concentration values in relation to the uncorrected concentration values. The greater accuracy and precision of the of the compensated analyte concentrations in relation to the uncompensated analyte concentrations is shown by the closer grouping around the zero combined bias line of FIG. 6F. These results establish that complex index functions are transferable between different samples and may be determined in the laboratory for later use in the measurement device.

Figure 7:
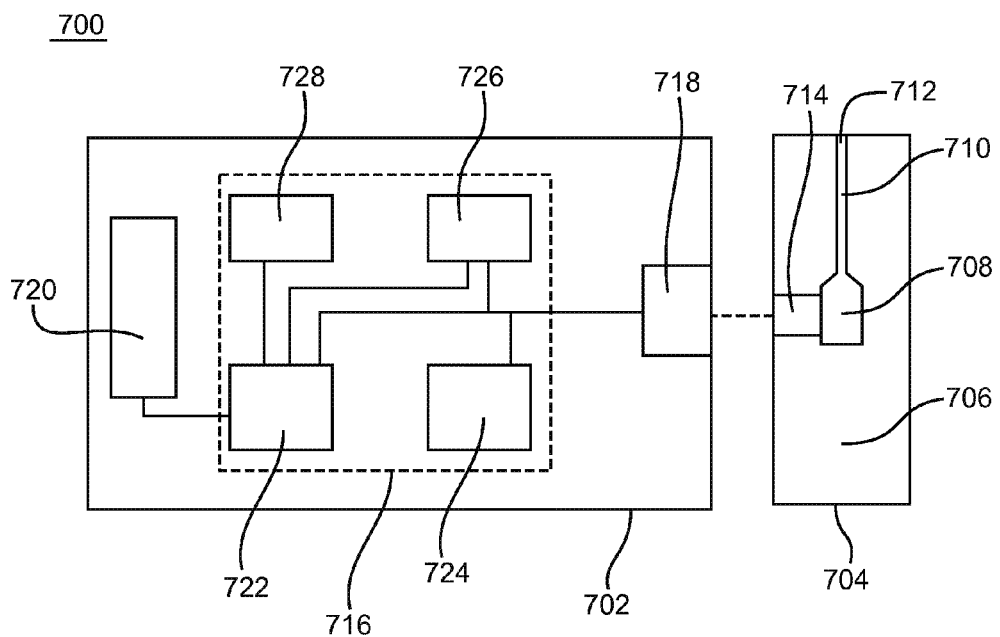
FIG. 7 depicts a schematic representation of a biosensor system that determines an analyte concentration in a sample of a biological fluid.

FIG. 7 depicts a schematic representation of a biosensor system 700 that determines an analyte concentration in a sample of a biological fluid. Biosensor system 700 includes a measurement device 702 and a test sensor 704, which may be implemented in any analytical instrument, including a bench-top device, a portable or hand-held device, or the like. The measurement device 702 and the test sensor 704 may be adapted to implement an electrochemical sensor system, an optical sensor system, a combination thereof, or the like. The biosensor system 700 adjusts a correlation for determining analyte concentrations from output signals with at least one $\Delta S$ value. The $\Delta S$ adjusted correlations may improve the measurement performance of the biosensor system 700 in determining the analyte concentration of the sample. The biosensor system 700 may be utilized to determine analyte concentrations, including those of glucose, uric acid, lactate, cholesterol, bilirubin, and the like. While a particular configuration is shown, the biosensor system 700 may have other configurations, including those with additional components.

The test sensor 704 has a base 706 that forms a reservoir 708 and a channel 710 with an opening 712. The reservoir 708 and the channel 710 may be covered by a lid with a vent. The reservoir 708 defines a partially-enclosed volume. The reservoir 708 may contain a composition that assists in retaining a liquid sample such as water-swellable polymers or porous polymer matrices. Reagents may be deposited in the reservoir 708 and/or the channel 710. The reagents may include one or more enzymes, binders, mediators, and like species. The reagents may include a chemical indicator for an optical system. The test sensor 704 also may have a sample interface 714 disposed adjacent to the reservoir 708. The sample interface 714 may partially or completely surround the reservoir 708. The test sensor 704 may have other configurations.

In an optical sensor system, the sample interface 714 has an optical portal or aperture for viewing the sample. The optical portal may be covered by an essentially transparent material. The sample interface may have optical portals on opposite sides of the reservoir 708.

In an electrochemical system, the sample interface 714 has conductors connected to a working electrode and a counter electrode. The electrodes may be substantially in the same plane or in more than one plane. The electrodes may be disposed on a surface of the base 706 that forms the reservoir 708. The electrodes may extend or project into the reservoir 708. A dielectric layer may partially cover the conductors and/or the electrodes. The sample interface 714 may have other electrodes and conductors.

The measurement device 702 includes electrical circuitry 716 connected to a sensor interface 718 and a display 720. The electrical circuitry 716 includes a processor 722 connected to a signal generator 724, an optional temperature sensor 726, and a storage medium 728.

The signal generator 724 provides an electrical input signal to the sensor interface 718 in response to the processor 722. In optical systems, the electrical input signal may be used to operate or control the detector and light source in the sensor interface 718. In electrochemical systems, the electrical input signal may be transmitted by the sensor interface 718 to the sample interface 714 to apply the electrical input signal to the sample of the biological fluid. The electrical input signal may be a potential or current and may be constant, variable, or a combination thereof, such as when an AC signal is applied with a DC signal offset. The electrical input signal may be applied as a single pulse or in multiple pulses, sequences, or cycles. The signal generator 724 also may record an output signal from the sensor interface as a generator-recorder.

The optional temperature sensor 726 determines the temperature of the sample in the reservoir of the test sensor 704. The temperature of the sample may be measured, calculated from the output signal, or assumed to be the same or similar to a measurement of the ambient temperature or the temperature of a device implementing the biosensor system. The temperature may be measured using a thermister, thermometer, or other temperature sensing device. Other techniques may be used to determine the sample temperature.

The storage medium 728 may be a magnetic, optical, or semiconductor memory, another storage device, or the like. The storage medium 728 may be a fixed memory device, a removable memory device, such as a memory card, remotely accessed, or the like.

The processor 722 implements the analyte analysis and data treatment using computer readable software code and data stored in the storage medium 728. The processor 722 may start the analyte analysis in response to the presence of the test sensor 704 at the sensor interface 718, the application of a sample to the test sensor 704, in response to user input, or the like. The processor 722 directs the signal generator 724 to provide the electrical input signal to the sensor interface 718. The processor 722 receives the sample temperature from the temperature sensor 726. The processor 722 receives the output signal from the sensor interface 718. The output signal is generated in response to the reaction of the analyte in the sample. The output signal may be generated using an optical system, an electrochemical system, or the like. The processor 722 determines $\Delta S$ compensated analyte concentrations from output signals using a correlation equation as previously discussed. The results of the analyte analysis may be output to the display 720 and may be stored in the storage medium 728.

The correlation equations between analyte concentrations and output signals may be represented graphically, mathematically, a combination thereof, or the like. A correlation equation may include one or more index functions. Correlation equations may be represented by a program number (PNA) table, another look-up table, or the like that is stored in the storage medium 728. Constants and weighing coefficients also may be stored in the storage medium 728. Instructions regarding implementation of the analyte analysis may be provided by the computer readable software code stored in the storage medium 728. The code may be object code or any other code describing or controlling the functionality described herein. The data from the analyte analysis may be subjected to one or more data treatments, including the determination of decay rates, K constants, ratios, functions, and the like in the processor 722.

In electrochemical systems, the sensor interface 718 has contacts that connect or electrically communicate with the conductors in the sample interface 714 of the test sensor 704. The sensor interface 718 transmits the electrical input signal from the signal generator 724 through the contacts to the connectors in the sample interface 714. The sensor interface 718 also transmits the output signal from the sample through the contacts to the processor 722 and/or signal generator 724.

In light-absorption and light-generated optical systems, the sensor interface 718 includes a detector that collects and measures light. The detector receives light from the liquid sensor through the optical portal in the sample interface 714. In a light-absorption optical system, the sensor interface 718 also includes a light source such as a laser, a light emitting diode, or the like. The incident beam may have a wavelength selected for absorption by the reaction product. The sensor interface 718 directs an incident beam from the light source through the optical portal in the sample interface 714. The detector may be positioned at an angle such as 45° to the optical portal to receive the light reflected back from the sample. The detector may be positioned adjacent to an optical portal on the other side of the sample from the light source to receive light transmitted through the sample. The detector may be positioned in another location to receive reflected and/or transmitted light.

The display 720 may be analog or digital. The display 720 may include a LCD, a LED, an OLED, a vacuum fluorescent, or other display adapted to show a numerical reading. Other displays may be used. The display 720 electrically communicates with the processor 722. The display 720 may be separate from the measurement device 702, such as when in wireless communication with the processor 722. Alternatively, the display 720 may be removed from the measurement device 702, such as when the measurement device 702 electrically communicates with a remote computing device, medication dosing pump, and the like.

In use, a liquid sample for analysis is transferred into the reservoir 708 by introducing the liquid to the opening 712. The liquid sample flows through the channel 710, filling the reservoir 708 while expelling the previously contained air. The liquid sample chemically reacts with the reagents deposited in the channel 710 and/or reservoir 708.

The test sensor 702 is disposed adjacent to the measurement device 702. Adjacent includes positions where the sample interface 714 is in electrical and/or optical communication with the sensor interface 718. Electrical communication includes the transfer of input and/or output signals between contacts in the sensor interface 718 and conductors in the sample interface 714. Optical communication includes the transfer of light between an optical portal in the sample interface 714 and a detector in the sensor interface 718. Optical communication also includes the transfer of light between an optical portal in the sample interface 714 and a light source in the sensor interface 718.

The processor 722 receives the sample temperature from the temperature sensor 726. The processor 722 directs the signal generator 724 to provide an input signal to the sensor interface 718. In an optical system, the sensor interface 718 operates the detector and light source in response to the input signal. In an electrochemical system, the sensor interface 718 provides the input signal to the sample through the sample interface 714. The processor 722 receives the output signal generated in response to the redox reaction of the analyte in the sample as previously discussed.

The processor 722 determines the analyte concentration of the sample. The measurement device adjusts the correlation between analyte concentrations and output signals with at least one $\Delta S$ value. The analyte concentration is determined from the slope-adjusted correlation and the output signal. As described previously, normalization techniques also may be used.

While various embodiments of the invention have been described, it will be apparent to those of ordinary skill in the art that other embodiments and implementations are possible within the scope of the invention.

What is claimed is:

1. A method for determining an analyte concentration in a sample, comprising:
    (a) applying the sample to a test sensor;
    (b) applying an electrical or optical input signal to the sample;
    (c) measuring at least one uncompensated output signal value i from the sample, wherein the value i is responsive to an undetermined concentration of the analyte in the sample;
    (d) determining at least one slope deviation ΔS value from a first complex index function f(CIndex) including at least a first term and a second term, wherein
    the first term includes a product of a first weighing coefficient and at least a first error parameter; and
    the second term includes a product of a second weighing coefficient and at least a second error parameter;
    (e) determining a corrected analyte concentration $A_{corr}$ in the sample from the at least one uncompensated output signal value by adjusting a previously determined reference slope $S_{cal}$ with the at least one slope deviation ΔS value and combining the adjusted slope with the at least one uncompensated output signal value,
    wherein steps (d) and (e) are performed by a processor using computer readable software code.

2. The method of claim 1, where the at least one slope deviation ΔS value is in a substantially linear relationship with a percent bias ((ΔA/$A_{ref}$)*100%) of the determined analyte concentration,
    wherein ΔA represents the difference between the corrected analyte concentration $A_{corr}$ and a reference analyte concentration $A_{ref}$.

3. The method of claim 1, wherein the previously determined reference slope $S_{cal}$ is pre-determined with a reference instrument.

4. The method of claim 1, wherein the at least one slope deviation value ΔS is represented as follows:

$$\Delta S = b_1 * f(CIndex) + b_0,$$

wherein $b_1$ represents a slope and $b_0$ represents a constant.

5. The method of claim 1, wherein the first complex index function f(CIndex) further comprises at least one constant that is not equal to zero.

6. The method of claim 1, wherein one of the first term and the second term includes a raw analyte concentration value of the sample.

7. The method of claim 1, wherein one of the first term and the second term includes a temperature.

8. The method of claim 1, wherein one of the first term and the second term includes an error parameter responsive to a % Hct of the sample.

9. The method of claim 1, wherein each of the first error parameter and the second error parameter is independently selected from intermediate output signal values and values external to the at least one uncompensated output signal value i.

10. The method of claim 9, wherein the first error parameter and the second error parameter are responsive to error contributors causing an alteration of the at least one uncompensated output signal value.

11. The method of claim 9, wherein the first error parameter and the second error parameter are independently responsive to different error contributors and each of the first error parameter and the second error parameter has an $R^2$ correlation with $\Delta S_{cal}$ of at least 0.3, wherein the $\Delta S_{cal}$ is represented as follows:

$$\Delta S_{cal} = \frac{i - Int}{A_{ref}} - S_{cal},$$

wherein $A_{ref}$ is a reference analyte concentration and Int is the intercept from a reference correlation equation.

12. The method of claim 1, wherein the at least one slope deviation ΔS value determined from the first complex index function f(CIndex) has an $R^2$ correlation with $\Delta S_{cal}$ of at least 0.6, wherein the $\Delta S_{cal}$ is represented as follows:

$$\Delta S_{cal} = \frac{i - Int}{A_{ref}} - S_{cal},$$

wherein $A_{ref}$ is a reference analyte concentration and Int is the intercept from a reference correlation equation.

13. The method of claim 2, wherein the determining the corrected analyte concentration $A_{corr}$ in the sample further comprises determining corrected analyte concentrations of multiple samples and the first complex index function f(CIndex) provides the corrected analyte concentrations determined of the multiple samples with a standard deviation value of less than 5 for the combined percent biases of the multiple samples.

14. The method of claim 13, wherein the determined corrected analyte concentrations of the multiple samples fall within a ±10% combined bias limit over the reference analyte concentrations.

15. The method of claim 13, wherein the determined corrected analyte concentrations of the multiple samples fall within a ±8% combined bias limit over the reference analyte concentrations.

16. The method of claim 13, wherein the determined corrected analyte concentrations of the multiple samples fall within a +5% combined bias limit over the reference analyte concentrations.

17. The method of claim 1, further comprising:
    a second complex index function, wherein different error parameters are transformed by the complex index function and the second complex index function to provide at least two slope deviation ΔS values; or
    an index function, where different error parameters are transformed by the complex index function and the index function to provide at least two slope deviation ΔS values.

18. The method of claim 1, further comprising normalizing the at least one slope deviation ΔS value, wherein the normalizing is in response to a slope of a reference correlation equation or in response to a normalized slope function.

19. The method of claim 1, further comprising previously identifying at least one exclusion value and applying an exclusion test to the at least one exclusion value to identify a term to exclude from the first complex index function f(CIndex).

* * * * *